United States Patent [19]
Garvey, III et al.

[11] Patent Number: 5,656,767
[45] Date of Patent: Aug. 12, 1997

[54] AUTOMATIC DETERMINATION OF MOISTURE CONTENT AND LUBRICANT TYPE

[75] Inventors: Raymond E. Garvey, III, Loudon; Alexander Andrew Carey, Lenoir City, both of Tenn.

[73] Assignee: Computational Systems, Inc., Knoxville, Tenn.

[21] Appl. No.: 614,817

[22] Filed: Mar. 8, 1996

[51] Int. Cl.$^6$ .................. G01N 27/22; E21B 43/12; G01R 27/22; G01F 1/74
[52] U.S. Cl. .................. 73/61.44; 324/324; 324/694; 324/664; 364/422; 364/510
[58] Field of Search .................. 73/61.44; 324/324, 324/698, 204, 658, 634, 689, 690, 694, 341; 340/631

[56] References Cited

U.S. PATENT DOCUMENTS

| | | | |
|---|---|---|---|
| 1,940,772 | 12/1933 | Schoenberg | 88/14 |
| 2,599,583 | 6/1952 | Robinson et al. | 175/183 |
| 2,889,736 | 6/1959 | Borg | 88/14 |
| 3,049,964 | 8/1962 | Miller et al. | 88/14 |
| 3,253,606 | 5/1966 | Kuntz | 137/115 |
| 3,371,574 | 3/1968 | Dwyer | 88/14 |
| 3,790,279 | 2/1974 | Skala | 356/70 |
| 3,892,485 | 7/1975 | Merritt et al. | 356/103 |
| 4,003,661 | 1/1977 | Yamano | 356/201 |
| 4,015,194 | 3/1977 | Epling | 324/1 |
| 4,029,554 | 6/1977 | Ellison | 204/1 T |
| 4,047,814 | 9/1977 | Westcott | 356/38 |
| 4,302,754 | 11/1981 | Magee et al. | 340/631 |
| 4,492,461 | 1/1985 | Jones et al. | 356/38 |
| 4,646,070 | 2/1987 | Yasuhara et al. | 340/603 |
| 4,677,847 | 7/1987 | Sewatari et al. | 73/64 |
| 4,692,698 | 9/1987 | Lewis | 324/204 |
| 4,701,713 | 10/1987 | Eaton et al. | 324/442 |
| 4,741,204 | 5/1988 | Luck et al. | 73/116 |
| 4,791,374 | 12/1988 | Yodice et al. | 324/439 |
| 4,796,204 | 1/1989 | Inoue | 364/550 |
| 4,815,536 | 3/1989 | Prendergast et al. | 166/250 |
| 4,831,362 | 5/1989 | Tsaprazis | 340/515 |
| 4,857,829 | 8/1989 | Sagae et al. | 324/61 R |

(List continued on next page.)

FOREIGN PATENT DOCUMENTS

| | | |
|---|---|---|
| 2165650 | 4/1988 | United Kingdom . |
| 2160655 | 5/1989 | United Kingdom . |

OTHER PUBLICATIONS

B. J. Roylance & A. L. Price, The Development Of A Computer–Aided Systemic Particle Analysis Procedure—CASPA, Dec. 1992 Lubrication Engineering, p. 940.

*Primary Examiner*—Hezron E. Williams
*Assistant Examiner*—J. David Wiggins
*Attorney, Agent, or Firm*—Luedeka, Neely & Graham, P.C.

[57] ABSTRACT

A method and apparatus for automatically detecting a lubricant type and the relative quantity of water present in a test sample of lubricating oil includes the use of an open grid capacitive sensor element that incorporates the lubricating oil as a dielectric medium. The sensor element grid is energized by a frequency variable oscillator that automatically responds to changes in the oil dielectric constant with corresponding frequency changes. As a reference, a sample of new or uncontaminated test oil is confined in wet surface contact with the energized, open grid sensor element. Oscillator frequency changes are measured and recorded, either continuously or at frequent intervals, over a standardized elapsed time interval to generate a reference characterization of the frequency-time relationship distinctive of the particular oil. The same is repeated for a sample of contaminated oil and a corresponding frequency-time relationship generated. Water affinity rate correlations between frequency change and respective states of moisture content are determined and data base recorded. The affinity rate correlations are applied to the respective frequency differentials between the contaminated oil and uncontaminated oil at the end of the test period. Data bases are also recorded of correlations between natural frequency and sample temperature changes that distinguish lubricants by type, use classification or quantity of additive content.

16 Claims, 13 Drawing Sheets

U.S. PATENT DOCUMENTS

| | | | |
|---|---|---|---|
| 5,067,345 | 11/1991 | Mougne | 73/61.1 R |
| 5,101,367 | 3/1992 | Agar | 364/551.01 |
| 5,132,903 | 7/1992 | Sinclair | 364/422 |
| 5,249,455 | 10/1993 | Cox | 73/61.44 |
| 5,259,239 | 11/1993 | Gaisford | 73/61.44 |
| 5,260,667 | 11/1993 | Garcia-Golding et al. | 324/694 |
| 5,272,444 | 12/1993 | Cox | 324/698 |
| 5,363,696 | 11/1994 | Cardellini et al. | 73/61.44 |

# 5,656,767

AUTOMATIC DETERMINATION OF MOISTURE CONTENT AND LUBRICANT TYPE

BACKGROUND OF THE INVENTION

1. Field of the Invention

This invention relates to a method and apparatus for detecting the lubricant type and degree of water contamination present in a lubricating oil. Additionally, the invention provides a method for classifying unknown oils as to additive content.

2. Description of the Prior Art

Lubricating oils serve multiple functions in mechanical systems. They reduce friction in each of the three lubrication regimes depending on application type: hydrodynamic, elastohydrodynamic, and boundary.

For applications with conformal bearings, such as Babbitt bearings, the lubricant transfers distributed loads, in the form of radial pressure, from shaft to sleeve. This is hydrodynamic lubrication and is similar to an automobile hydroplaning on wet pavement.

For highly loaded rolling element bearings such as gears and anti-friction bearings, the viscosity of a protective lubricant must increase exponentially with pressure which results from forcing the lubricant into the small clearance between the rolling element and the raceway. The lubricant viscosity increases until the oil has the bulk modulus-of-elasticity of a solid, able to transmit highly concentrated loads. This form of lubrication, elastohydrodynamic, practically eliminates metal to metal contact with extremely low friction energy losses.

For traction type applications such as slides and wheels, lubricant serves to reduce wear due to sliding contact and abrasion. In this case, the physical loads are transmitted through metal to metal contact. The traction or friction in this type system can be very high, with coefficients of sliding friction as high as ⅓ of the normal force that presses the two components together. The friction, wear and traction may be greatly reduced by lubricating the surfaces so that only a limited amount of shear can be transmitted between components. This can be done with either solid lubricants such as Teflon, molybdenum disulfide or graphite or with liquid lubricants formulated with extreme pressure and anti-wear additives.

In addition to these requirements for transferring loads, reducing friction, and minimizing wear, lubricants fulfill several other functions critical to machine life. These include sealing surfaces from corrosion and other forms of chemical attack, transmitting hydraulic power, cleaning away contaminants and wear debris, cooling hot surfaces and electrically isolating and insulating dissimilar metals from galvanic interaction. In the special case of electric transformer applications, oil provides cooling and electrical isolation (i.e., a low dielectric medium).

Moisture contamination of lubricating oil is a frequent and serious problem for many industrial plant applications. Moisture causes problems by rendering the oil additives ineffective, by corroding metal surfaces, and by incapicating elastohydrodynamic lubrication. Sources of oil contamination by water include the environment (humidity, rain and condensate for example), process materials (fluids and steam) and facility cleaning operations.

Since water is substantially immiscible with petroleum oil, chemically free water, in fluid presence with oil, stratifies in the low points of a reservoir or circulation system. If the system is turbulent, such free water may entrain the oil as droplets. In either case, the water displaces the oil to prevent the lubrication function of the oil and jeopardize the mechanical system. Moisture also chemically reacts with many oil additives otherwise intended to provide antiwear, antioxidation, extreme pressure (EP), anti-foaming and detergency functions. Furthermore, moisture consumes all or part of the dispersant and emulsifier additives intended to prevent contaminants from coalescing or agglomerating.

It is well known that moisture promotes corrosion of metal surfaces. The polar nature of the water molecule supports ionic mobility and encourages chemical attack to copper, lead and other reactive metal surfaces, particularly in the presence of air. Moisture also supports electrochemical interaction between galvanically dissimilar oil wetted parts.

As mentioned previously, elastohydrodynamic lubrication depends on the unique pressure-viscosity property of mineral oils and synthetic lubricants. Free water droplets are unable to maintain physical separation between rolling elements or between gear teeth under these extremely high pressures. The resulting impacts cause surface damage and shorten component life.

There are three forms or states in which water is found when combined with oil. The water can be dissolved in the oil in the sense that it is hydrated, dissolved or reacted with additives that are mixed with the oil. In another state, oil can be dispersed or emulsified with the oil. Finally, it can be independently stratified or mixed as free water droplets which are separate from the oil. Each of these states damages the oil and the mechanical system in a different way.

Water is a polar molecule whereas hydrocarbons are non-polar. Since 'like dissolves like' the solubility of water in hydrocarbons is small. As the size of the hydrocarbon increases (that is the number of carbon atoms in the chain), the water solubility decreases. Aromatic hydrocarbons will have a higher water solubility than paraffinic hydrocarbons. Therefore, hydrocarbon oils will have water solubilities from less than 1 to about 100 ppm.

Oils used in industry may contain additives or be entirely synthetic (e.g. PAG, esters etc.). Generally the water solubility increases with increasing oxygen content based on elemental analysis. An oil dielectric constant also increases with increasing oxygen content. A more sophisticated analysis would include contributions from sulfur, phosphorous and metals. These minor constituents would increase the dielectric constant and increase the solubility of water. A rough rule of thumb is that as the dielectric constant increases, the water solubility should also increase.

Moisture dissolved in the oil consumes performance enhancing additives and promotes corrosion. Reaction of water with oxidation inhibitors produces acids and precipitates. These water reaction products increase wear and interferences. At high operating temperatures (above 60° C.), water reacts with and destroys zinc type antiwear additives. For example, zinc dithiophosphate (ZDTP) is a popular boundary lubricant added to hydraulic fluid to reduce wear in high pressure pumps, gears and bearings. When this type additive is depleted by reacting with water, abrasive wear accelerates rapidly. The depletion shows up as premature component failure resulting from metal fatigue and other wear mechanisms. Other reactions produce extreme pH compounds which secondarily react with metal components of the machine the lubricant is intended to protect.

Emulsions are "significantly stable" complexes of two immiscible liquids. The term "significantly stable" relates to intended use and may range from a few minutes to years. Two types of emulsions are recognized: macroemulsions and microemulsions. Macroemulsions, which are more common, range from 0.2 to 50 micrometers and are easily visible under a microscope. Microemulsions range from 0.01 to 0.2 micrometers and are not visible Under a microscope. The size of the dispersed particles in an emulsion determines its appearance to the naked eye. The diameter of the dispersed particles in an emulsion determines its appearance to the naked eye. If the diameter of the dispersed particles is 1 micrometer, it appears milky white; 1–0.1 micrometers, blue white; 0.1–0.5 gray and semitransparent; <0.05 micrometers it is transparent (Surfactants and Interfacial Phenomena, M J Rosen, John Wiley & Sons, 1979, p224). The smaller the range of sizes of droplets in the emulsion, the more stable it is. Thus, macroemulsions are opaque and microemulsions are transparent to semitransparent to visible light.

Two immiscible pure liquids can not form a 'stable' emulsion. In order to form a stable emulsion, a third component or an emulsifying agent must be added. This agent may be a surfactant, although surface active agents may include finely divided solids. Frequently the most effective emulsifying agents are mixtures of two or more substances which act synergistically. The most common combination of emulsifying agents are a water soluble surfactant mixed with an oil soluble surfactant.

Water emulsified with oil consumes nearly all remaining additives, increases corrosion and changes fluid viscosity (normally increasing it). Systems designed to operate with water present must either emulsify or demulsify the water to extend life of the mechanical parts. Automotive applications must emulsify the water until it can be driven off by heat. Steam turbines typically demulsify water, dropping it out in the oil compartment. In either of these cases, water left in the system can lead to corrosion and even microbial growth. Under certain conditions, bacteria can live and reproduce very rapidly when sufficient water is present in oil. These living organisms can ruin the oil system by clogging filters, changing water emulsion characteristics, increasing corrosion rates and producing acidic waste products.

Free water forms from the coalescing of emulsified water. It is the thermodynamically stable state with oil that, is supersaturated with water. In oils with no additives (e.g. turbine oils), free water forms rapidly. In oils with additives that form stable emulsions, free water forms after the emulsifying agent is saturated by water. Free water droplets are desirable in some lubricating systems (those designed to demulsify water) and very detrimental in others.

In mineral oils and polyalphaolephin (PAO) synthetic hydrocarbon oils, additives are required,for any significant amount of water either to be dissolved in oil or to be emulsified with oil. Pure mineral oils are saturated with as little as 1 ppm water, and turbine oils saturate with as little as 100 ppm water. Above saturation level, water coalesces into free water droplets eventually settling to the bottom of the oil compartment. This is a very desirable characteristic for most steam turbines and paper machines. In these applications, water contamination is common. So to avoid the consequences of moisture retention in these machines, oils are designed to demulsify, or drop water out in the oil compartment before returning to the machine. Periodically, water is bled off from the bottom of the oil compartment (e.g., sump). Demulsibility of oil is good if water Separates quickly at operating temperatures. It is bad if it separates slowly. Oils designed to demulsify oil are normally pure mineral oil or PAOs with very little additive.

Engine oils and most other industrial lubricants will tend to emulsify rather than demulsify water. In these lubricants the additives serve to disperse water and prevent it from coalescing into free water droplets.

Additives modify the solubility and emulsion character of mineral oils. Transformer oils are saturated with <1 to 3 ppm water. Oil-based hydraulic fluids are typically saturated with 100 ppm (0.01%) to 1000 ppm (0.1%) water Industrial lubricants are typically saturated with 600 ppm (0.06%) to 5000 ppm (0.5%) water. Automotive lubricants are typically saturated with 1% to 5% water. Stern tube oils (those used to lubricate the aft bearing on a ship propulsion shaft), have increasing amounts of additive, particularly increasing amounts of total dispersant, detergent, anti-oxidant, anti-wear and extreme pressure compounds.

Many methods and devices have been developed to detect the contamination or breakdown of oil. One such device, shown in U.S. Pat. No. 4,646,070 issued to Yasuhara, discloses a device for detecting deterioration in lubricating oil which comprises a pair of capacitor electrodes positioned in the lubricating oil. The device uses the oil as a dielectric between the electrodes to develop a voltage frequency signal across the sensor capacitor thus determining the dielectric number of constant and deterioration of the oil. A major drawback of this device and others is that they do not inform the tester of the Specific type or magnitude of deterioration in the system.

Other methods of oil analysis comprise the preparation of microscope slides whereby particles are counted, measured and visually evaluated for subjective clues to wear, breakage and failure. Although effective, this type of analysis is both slow and expensive.

Lubrication oil is frequently blended with non-petroleum additives such as detergents to modify the oil properties. In the presence of water, these additives may combine with water, either reactively in solution or passively as emulsions. In either case, the additives are prevented from their objectives of improving the lubrication properties.

When water is present in a lubrication oil system, it is useful to know the quantity and form of such water. Moisture in solution may be measured using a wet chemistry filtration method. Although effective, this type of analysis is both slow and expensive.

It is, therefore, an objective of the present invention to provide a method and apparatus for quickly identifying the presence of moisture in a lubrication oil system.

Another object of the invention is to provide a method and apparatus for identifying the solution dispersed or free form that moisture in a lubrication system may be found.

Another object of the invention is to provide a method and apparatus for identifying the percentage of moisture in a lubrication system in each of three states of combination.

Another object of the invention is to classify the type of lubricant for the purpose of automatic oil analysis based on dielectric number or dielectric change due to temperature.

SUMMARY OF THE INVENTION

The present invention provides an apparatus for monitoring the condition of lubricating oil, preferably for the possible presence of corrosive products, contamination such as water, non-ferrous wear debris, and ferrous wear debris in the oil The apparatus includes a sample vessel for holding a sample volume of the tested lubricating oil in wet contact With a capacitance sensor. Optional magnet means induces an alternating magnetic field into the sample volume of lubricating oil while confined within the vessel in order to discount the effects of iron on the water measurement. An oscillator circuit measures capacitance as a function of the dielectric constant value of the tested oil.

The sensor means preferably includes a sensor element, a means for monitoring the output of the sensor, and a means for processing the sensor's output. The sensor element is physically arranged to support the sample volume of oil as the bottom of the sample vessel whereby gravity wets the sensor element surface with the oil sample and contaminants having a greater density than the oil tend to settle by gravity onto the surface of the sensor element. This sensor element surface includes at least two electrical conductors secured to a nonconductive substrate in a manner that when the surface is supporting the oil sample volume the oil provides an insulating dielectric medium between the conductors. Thus, the sensor acts as a capacitor and its capacitance varies in relation to at least the area of the conductors, the distance between the conductors, the dielectric constant and other properties of the oil. This relationship between the sensor and the lubricating oil allows the determination of the properties of the oil as it is influenced by the magnetic field.

In the preferred embodiment, the processing means of the invention-determines the amount and type of moisture contamination in the oil by comparing the capacitance of the sensor when exposed to a test oil sample to the capacitance of the sensor when exposed to a pure reference sample of the type of oil tested. The capacitance of the sensor is a relative measure of the dielectric constant for the oil covering the space between the capacitor conductors. A low relative dielectric constant for the oil produces a low capacitance for the sensor, which in turn causes a high natural frequency for the oscillator circuit. This is the case when fresh, uncontaminated oil is placed on the sensor. The natural frequency is relatively high because the oil is a very good insulator (e.g., it has a very low dielectric constant, less than 2.5). On the other hand, when water is present on the sensor surface, the capacitance increases and the natural frequency drops.

The apparatus electromagnet has a primary function of assisting with measurement of the ferrous wear debris particles. However, the electromagnet also plays an important role with respect to water measurement as a test Sample heater. Operation of the electromagnet heats the oil test sample approximately 1.0° C. during a 500 second test interval, for example. This slight heating triggers a change in dielectric value as a function of temperature which can be used to identify the type or class of lubricant. Each class of lubricant has a different affinity for water due to its base oil and additive composition. The value of the dielectric constant for a lubricant can be used to estimate the water solubility for that lubricant. This correlation results from the fact that dielectric constant increases for lubricants with an increased content of oxygen containing compounds. These same compounds have affinity for water.

A greater Capacitance in the test oil (relative to the calibration oil) that remains relatively constant over time indicates the presence of corrosive, products. A steady increase of the sensor's capacitance. While exposed in wet contact to the test oil indicates the presence of contamination in the oil. A fluctuating increase of the sensor's capacitance while exposed to the test oil indicates the presence of ferromagnetic particles in the oil. The changing polarity of the electromagnet causes the ferromagnetic particles to reorient thereby fluctuating the increase of the sensor's capacitance.

As file data, an experimentally based correlation is developed between the oscillator frequency responses to respective types of uncontaminated oil of known additive content while Wetting the sensor surface over a standardized test interval.

Experimentally developed file data is also prepared for the same or similar oils of known additive and total moisture content.

A well-mixed, contaminated oil of known additive content but unknown moisture content is tested in wet contact with the sensor element and optional energized electromagnet over the standardized test interval. The natural frequency of the oscillator at the start of the test interval is compared to the oscillator natural frequency from the similar uncontaminated oil. Any frequency differential at this point in the test sequence is related exclusively to additive dissolved water. The percentage quantity of water in solution with the test volume additives is determined from the experimentally developed file data.

As the test sequence proceeds over the standardized test interval, the natural frequency of the oscillator changes due to heating of the test oil by the electromagnet or an alternate heat source, and due to settlement and consolidation of dispersed water. Normally, such changes will cause a natural frequency decline as the dielectric value and capacitance increases. Oscillator natural frequency reduction at a steady, orderly rate is attributed to dispersed or emulsified water. Abrupt frequency reductions are attributed to free water droplets contacting and shorting the sensor grid.

Relating the oscillators frequency file data at the end of the standardized test interval respective to the uncontaminated reference oil at the oscillator frequency produced by the settling oil at the end of the standardized test interval provide a total frequency differential. This total frequency differential is approximately related to the total water content contaminating the oil sample. Furthermore that proportion of the total frequency differential quantity corresponding to abrupt changes in the rate of frequency decline also corresponds to the free water proportion of total water. Similarly, that proportion, of the total frequency differential corresponding to a steadily declining frequency also corresponds to the dispersed water proportion of total water.

This analytical approach is partially reversible and frequently offers a reliable data model by which the type and additive constituency of a test oil may be assumed. The service in which a lubricant is employed frequently either requires or suggests the presence of certain oil properties and characteristics. The pattern of a time-frequency correlation for a contaminated oil of known service often reveals the type and approximate, additive constituency of the same but uncontaminated oil.

Further details and advantages of this apparatus will become more apparent in the following description and the accompanying drawings.

BRIEF DESCRIPTION OF THE DRAWINGS

The present invention may best be understood by reference to the Detailed Description of a preferred embodiment when considered in conjunction with the Drawings in which.

DETAILED DESCRIPTION OF THE PREFERRED EMBODIMENT

Figure 1:
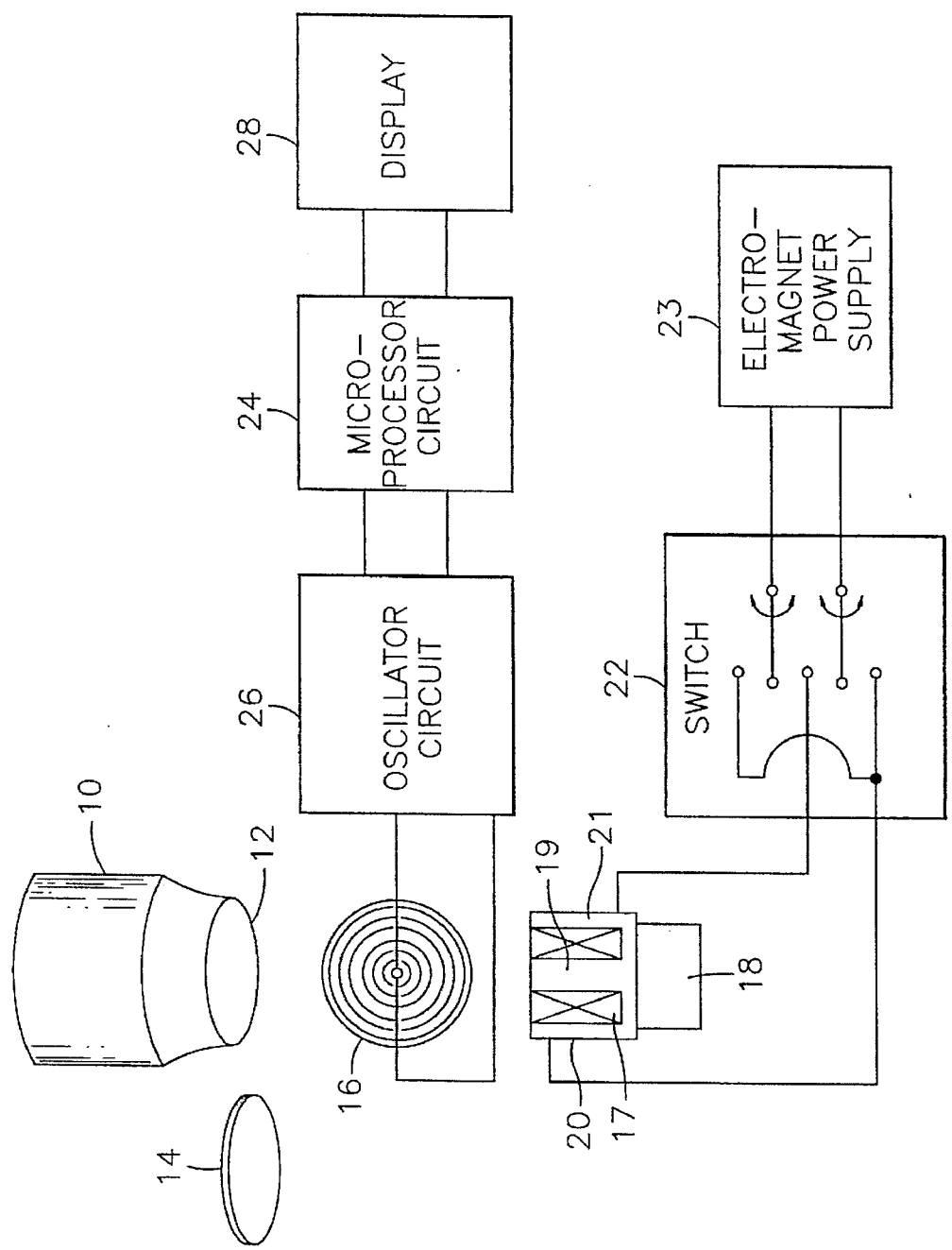
FIG. 1 is a diagrammatical block diagram of a preferred embodiment of the invention equipment.

Referring now to the drawings wherein the representations depict the preferred embodiment, there is shown in FIG. 1 a container 10 for holding a sample of lubricating oil that is to be tested. The container has an open mouth 12 and a removable and resealable lid 14 for sealably attaching over the mouth 12. For testing an oil sample, the sample charged container 10 is sealed closed by attachment of the lid 14 to the container mouth 12 and the container inverted to position the lid 14 below the container 10. This position allows the oil to flow down into direct wetted contact with the surface of sensor element 16. Furthermore, this measurement position allows gravity to influence the oil sample held in the container 10 thereby causing any contaminants in the oil to migrate downwardly toward the upper support surface of sensor element 16.

In FIG. 1, the sensor element 16 is symbolically represented and is shown removed from the mouth 12 for clarity of illustration. It will be understood that the sensor element 16 seals against the mouth 12 to close the container 10 and contain the oil.

An optional electromagnet 20 is placed vertically beneath and coaxially with the sensor element 16. This electromagnet 20 comprises an axial rod core 19 and a cylindrical case 21. Electrical windings 17 occupy the annulus between the rod 19 and the case 21. An optional permanent magnet 18 is located axially beneath and in direct contact with the optional electromagnet 20 to take advantage of the electromagnet core rod 19 for projecting the permanent magnet field along the core rod axis. The field of the electromagnet 20 acts in conjunction or opposition to the permanent magnet 18 depending on the polarity of the electromagnet 20. The electromagnet 20 is electrically connected to switch 22 which is in turn electrically connected to an electromagnet voltage supply 23. The switch 22 and the electromagnet voltage supply 23 allow the electromagnet to be turned on in a north-south orientation, turned on in a south-north orientation, or turned off. The switch 22 in the preferred embodiment is electrically connected to a microprocessor circuit 24 which controls the change in the polarity of the electromagnet 20 as well as the rate at which the electromagnet 20 is turned on and off, which is preferably about one (1) cycle per second. In this embodiment, the electromagnet 20 is a model EMR75 manufactured by Miami Magnet Company operating at 12 volts and about 750 milliamps. The permanent magnet 18 has a diameter of one inch, a thickness of one quarter (¼) inch and a strength that about matches electromagnet 20.

The sensor element 16 is electrically connected to an oscillator circuit 26 which uses the sensor 16 as a capacitor to generate an output signal at a natural frequency corresponding to the capacitance. The oscillator circuit 26 is electrically connected to the microprocessor circuit 24 which uses the generated signal frequency to determine the presence and magnitude of corrosive products, contamination, and ferromagnetic particles in the oil. The microprocessor 24 is electrically connected to the display 28 which outputs the results of the microprocessor's determinations.

Figure 2:
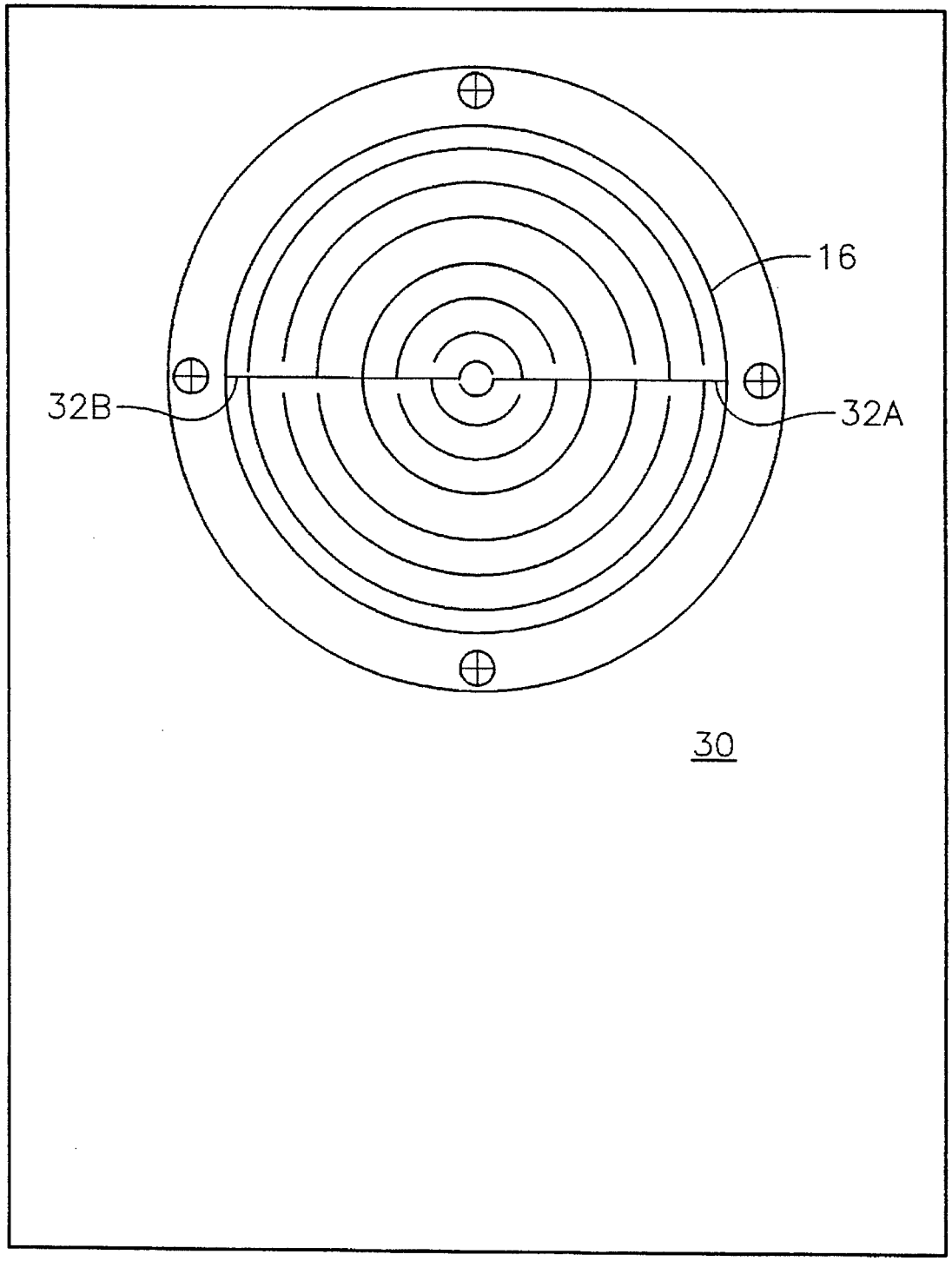
FIG. 2 is a plan view of the present invention sensor element.

FIG. 2 depicts an enlarged, somewhat diagrammatic, top view of the preferred embodiment of the sensor 16 as mounted to the test box 30 which also contains the permanent magnet 18, the electromagnet 20, the switch 22, the electromagnet voltage supply 23, and the oscillator circuit 26 of FIG. 1. The preferred sensor element 16 is Constructed in a open grid-like formation and is formed from two conductors 32a and 32b having extensions forming concentric half circles. Preferred fabrication technology is drawn from printed circuit manufacture whereby a thin film of electrically conductive material such as copper, silver or gold is deposited upon an insulating structural substrate such as fiberglass, alumina ceramic or beryllia ceramic. Photo masking procedures permit a precisely delineated removal of undesired film by chemical etching to leave the conductive film material in the illustrated grid pattern as conductors 32A and 32B. The remaining conductive grid may be protected from corrosion by a coating of gold or of lead and tin. The oil which wets the sensor 16 surface acts as the insulating dielectric medium between the conductors 32a and 32b. Thus, the conductors 32a and 32b act as capacitor plates with the capacitance varying with, at least, the area of the conductors 32a and 32b, the distance between the conductors 32a and 32b, and the dielectric constant of the oil. Numerous capacitance type sensors could be used, but in this embodiment, the sensor has a diameter of about 250 microns and are spaced apart a distance of about 250 microns; and the sensor 16 has a capacitance in air of about 30 picofarads.

Figure 3:
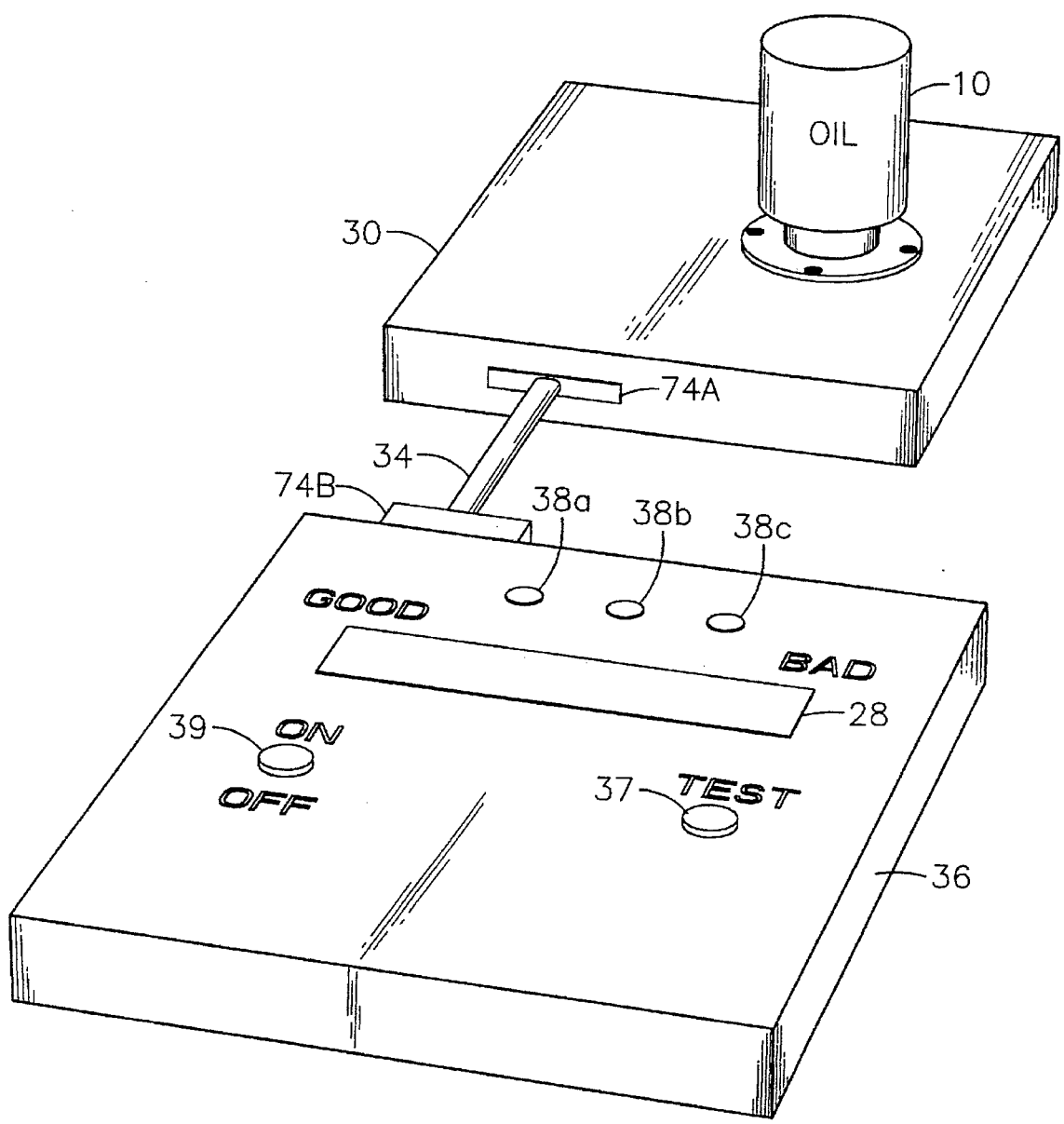
FIG. 3 is a perspective view of the invention equipment combined with a microprocessor unit.

FIG. 3 depicts an external, somewhat diagrammatic, view of the preferred embodiment of the apparatus. The container 10 is shown in the measurement position on the test box 30. A shielded serial cable 34 electrically connects the components in the test box 30 at connector port 74a to those components in the display box 36 by means of Connector port 74b. The display box 36 encloses the microprocessor 24 of FIG. 1. The display 28 is preferably an LCD display for displaying the value of contamination, corrosion and ferromagnetic particle levels. The display 28 is mounted on the display box 36 and is electrically connected to the microprocessor 24 within the box. Further depicted are three LEDs, 38a, 38b and 38c, that are electrically connected to the microprocessor 24 within the display box 36 and energized according to the changing levels of corrosion, contamination or ferromagnetic particles.

Figure 4:
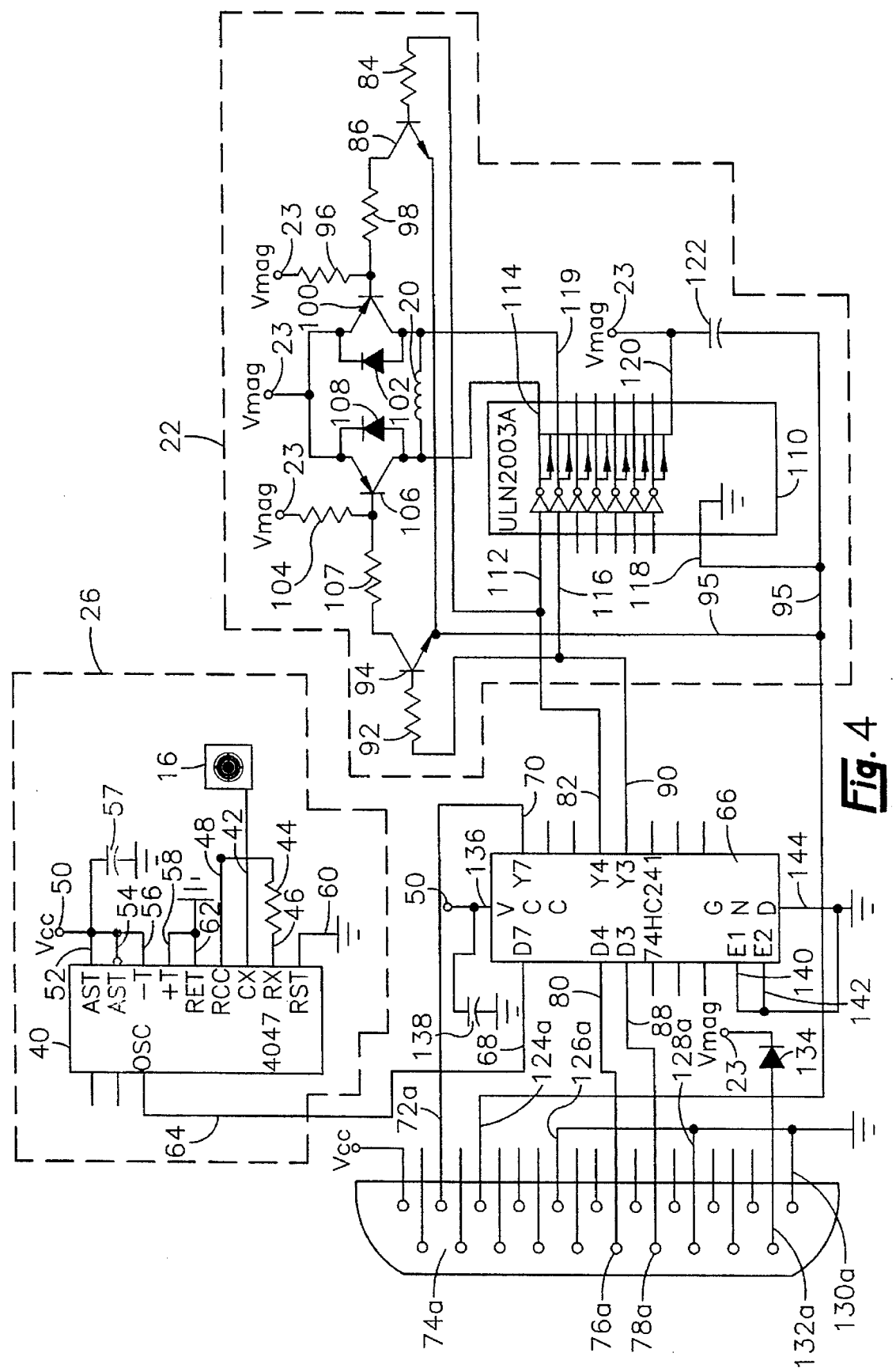
FIG. 4 is a Circuit diagram of the sensor element and associated analog circuit.

FIG. 4 depicts the preferred embodiment of the internal circuitry of the test box 30 shown in FIG. 3. The oscillator circuit 26 performs the function of generating a frequency pulse based upon the capacitance of the sensor 16. The oil in the sensor 16 acts as the dielectric medium, thereby altering the capacitance of the sensor. The capacitance increases as the dielectric constant increases (see Formula 1) causing an overall decrease in the natural frequency produced by the oscillator circuit 26 (see Formula 2).

$$C = k*E*(A/d) \qquad \text{Formula 1}$$

Where: C=capacitance of the sensor 16; k=the dielectric constant of the oil in the sensor 16; E=amount of energy stored; A=the surface area of the sensor 16; and, d=the distance between the sections of the sensor.

$$f_n = 1/(2\pi \sqrt{LC}) \qquad \text{Formula 2:}$$

Where: $f_n$=natural frequency at which circuit will oscillate if not acted upon by an external disturbance, Hz; C=capacitance, farads; L=inductance, henry.

The presence of polar oxides in the oil causes an increase in the dielectric constant, k. Additionally, since water has a higher dielectric constant than oil, its presence in the oil will cause an increase in the dielectric constant of the oil as the water settles into the vicinity of the sensor element 16 to displace oil from between the conductors 32A and 32B. If a substantial quantity of water accumulates on the sensor 16, it can cause the sensor 16 to be shorted. The presence of ferromagnetic particles 15 in the oil also causes an increase in the capacitance of the sensor 16 because the accumulation in particles on the sensor increases the sensor's surface area and capacitance in accordance with Formula 1.

The sensor element 16 is connected to a pin 42 of a monostable multivibrator 40 and is connected in parallel with the resistor 44 to pin 46 and pin 48 of the monostable multivibrator 40. A constant voltage source 50 is connected to pins 52, 54 and 56 of the monostable multivibrator 40 while pins 58, 60 and 62 are grounded. Pins 52, 54 and 56 are also connected to ground through a, preferably, 0.1 microfarad capacitor 57. Thus, sensor 16 is a variable capacitor connected in an R-C circuit to influence the frequency of the signal (pulses) transmitted from pin 64. The preferred monostable multivibrator is a general CMOS logic chip Model 4047. The oscillator circuit is trimmed to a natural frequency of about 60,000 Hz with the sensor element 16 wetted by uncontaminated kerosene.

The pin 64 which carries the oscillator signal pulses is connected to a pin 68 of a non-inverting buffer chip 66 which isolates the signal and outputs it from pin 70. The pin 70 is connected to a pin 72a of a connector port 74a. A signal is thereby sent through the connector port 74a along the signal cable 34 of FIG. 3 to an identical connector port 74b of the display box 36 of FIG. 3.

The connector port 74a also receives signals from the microprocessor 24 from pins 76a and 78a of the connector port 74a. These signals control the switch 22 from changing the polarity of the electromagnet 20 and for turning the electromagnet 20 on or off. As the permanent magnet 18 continuously attracts ferromagnetic particles 15 onto the surface of the sensor 16, the electromagnet, when turned on in opposition to or reinforcing the permanent magnet 18, will cause the particles 15 on the sensor element surface to shift thereby changing the surface area of the sensor which results in an altered frequency output from the monostable multivibrator 40. Thus, the electromagnet will cause a fluctuation in output pulses as its polarity is changed if ferromagnetic particles are present in the oil.

In the preferred embodiment, the electromagnet's polarity is cycled from an "off" state to a N-S polarity to a S-N polarity to produce the maximum fluctuation of particles 15 while continuously attracting particles with the permanent magnet 18. Persons knowledgeable in the art will further understand that total reversal of the polarity of the electromagnet is not required.

The pin 76a of connector port 74a is connected to a pin 80 of the buffer chip 66 which isolates the switching signal and outputs it from pin 82. The pin 82 is connected in series with a resistor 84 to the base of an NPN transistor 86. The pin 78a of connector port 74a is connected to pin 88 of the buffer chip 66 which isolates the signal and outputs it from the pin 90. The pin 90 is connected in series with a resistor 92 to the base of an NPN transistor 94. The emitters of the transistors 86 and 94 are tied together and attached to a signal ground wire 95 which acts to reduce noise in the system. The collector of transistor 86 is connected in series through resistors 96 and 98 to the electromagnet power supply 23, which provides $V_{mag}$, and further connected through resistor 98 to the base of a PNP transistor 100. A diode 102 is coupled across the emitter and collector of transistor 100 thus acting as a protection device for transient relief. The emitter of transistor 100 is further connected to the electromagnet voltage supply 23, and the collector of transistor. 106 is further coupled to the electromagnet 20. The collector of transistor 94 is connected in series to the electromagnet power supply 23 through resistors 104 and 107 and is further connected to the base of a PNP transistor 106 through resistor 107. A diode 108 is coupled across the emitter and collector of transistor 106 thus acting as a protection device for transient relief. The emitter of transistor 106 is further connected to the electromagnet voltage supply 23 (preferably a battery), and the collector of transistor 106 is further connected to the electromagnet 20.

The pin 82 of the buffer chip 66 is also coupled with a pin 112 of a Darlington driver chip 110 which operates as a current sink, dependent upon the logic level, and is connected from pin 114 to the electromagnet 20 in conjunction with the collector of transistor 106. The pin 90 of buffer chip 66 is connected to a pin 116 of the driver chip 110 which is in turn coupled from pin 118 to the electromagnet 20 in conjunction with the collector of the transistor 100. This configuration allows the current flow to the electromagnet 20 to be alternated or shut off completely by the microprocessor 24 thus providing the switch 22.

The driver chip 110 is connected to the signal ground wire 95 through a pin 118 and is connected to the electromagnet voltage supply 23 through a pin 120 which is further coupled through a series capacitor 122 to the signal ground wire. The signal ground wire 95 is connected to pin 124a of the connector port 74a.

The connector port 74a has pins 126a, 128a, and 130a connected to ground and has pin 132a connected through a diode 134 to the electromagnet power supply 23.

The buffer chip 66 has pin 136 connected to the constant voltage source 50 which is in turn coupled to ground through capacitor 138. The buffer chip also has pins 140, 142 and 144 coupled to ground.

Figure 5:
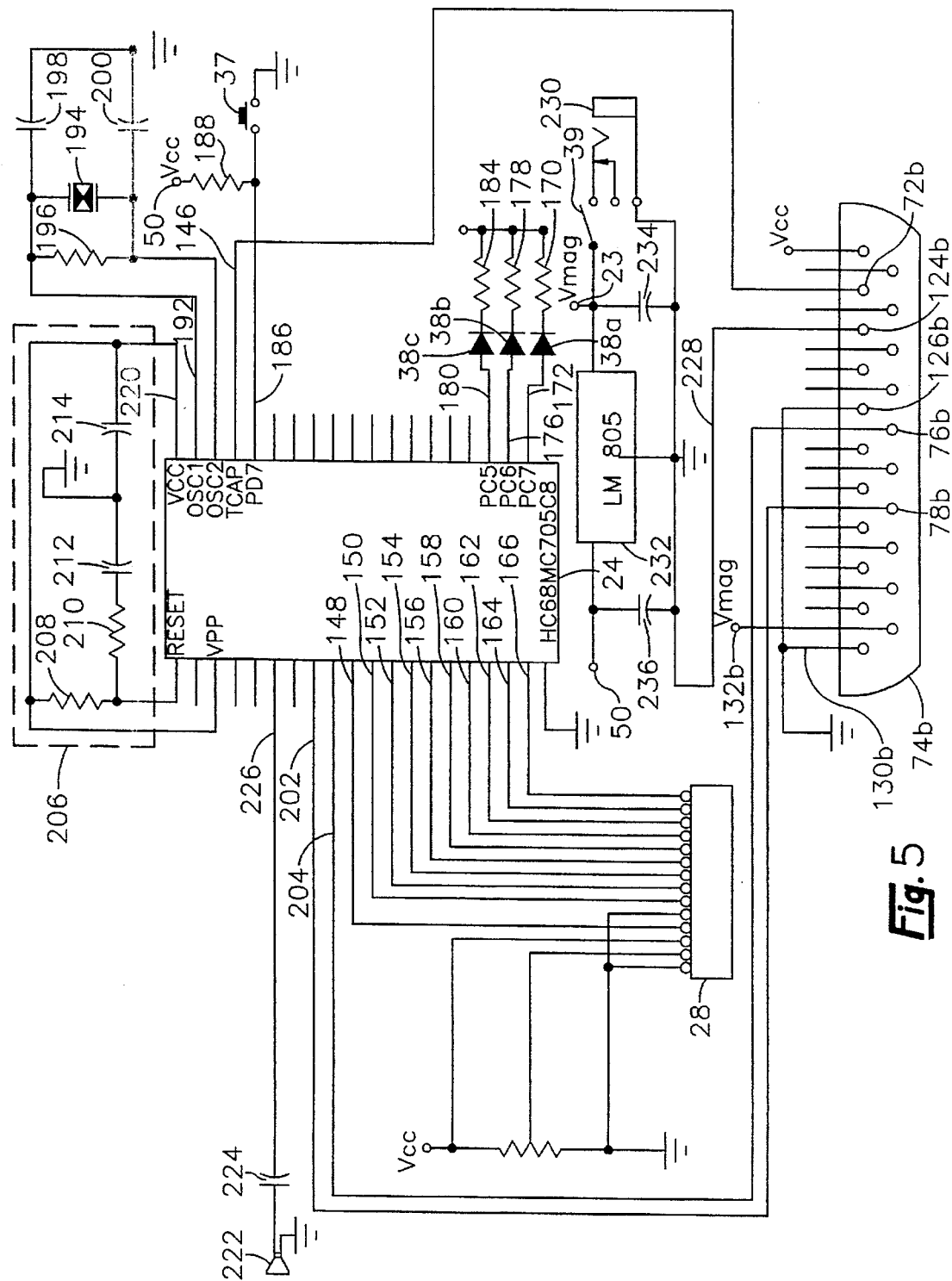
FIG. 5 is a circuit diagram of the microprocessor and associated circuitry that monitors the sensor and produces an output.

FIG. 5 depicts the internal circuitry of the display box 36 of FIG. 3. The connector port 74b connects the test box 30 to the shielded serial cable 34. The pin 72b carries the oscillator pulse and is connected to the microprocessor 24 at pin 146. The preferred microprocessor is an HCMoss microcontroller unit model MC68HC705C8 with erasable programmable read only memory. The microprocessor 24 counts the number of pulses produced by the multivibrator 40 per unit of time to establish a raw data count source which may be a ratio of the actual frequency generated by the multivibrator. For example, the microprocessor may register a data count at the uniform time interval of 0.1 sec. Consequently, a data count of 5000 corresponds to a multivibrator pulse frequency of 50,000 Hz. The data count and hence, frequency of the multivibrator 40 is inversely related to the amount of contamination, corrosive products and ferromagnetic particles in the test oil.

The microprocessor controls the polarity and the power to the electromagnet 20 by output signals from pins 202 and 204 which are connected to pins 76b and 78b of the connector port 74b. Thus, the signals are transferred along the shielded serial cable 34 to the connector port 74a of the test box 30. A low signal generated on both pins 202 and 204 will force the electromagnet 20 into its "off" mode. A high signal generated upon pin 202, while a low signal is generated on 204, will force the electromagnet into the "on" mode in north-south polarity. Finally, a high signal generated upon pin 204, while a low signal is generated on pin 202, will force the electromagnet into the "on" mode in south-north polarity.

A reset circuit 206 including resistors 208 and 210 connected to capacitors 212 and 214 is attached to the constant voltage source 50 and acts to pull up the input voltage to five volts after the supply contact is made. The reset circuit 206 is attached to pins 216, 218 and 220 of the microprocessor 24, thereby assuring that the internal reset of the microprocessor is working properly.

In the preferred embodiment, a beeper alarm 222 is used for signaling the presence of dangerous levels of deterioration and contamination in the test oil. The beeper 222 is attached through a capacitor 224 to a pin 226 of the microprocessor 24.

The connector port 74b has a pin 124b connected to a probe ground wire 228 which is connected to a power clip 230 for hook up to an external power source. The switch 39 engages the external power source when depressed thereby powering the electromagnet voltage supply 23. The switch 39 is further connected to a voltage regulator 232 which regulates the voltage to five volts for supplying the constant voltage source 50 which powers the digital requirements of the system. The electromagnet voltage supply 23 is connected to the probe ground wire 228 through resistor 234, and the constant voltage source 50 is similarly connected to the ground wire 228 through resistor 236.

The connector port 74b has pins 126b and 130b connected to ground. The connector port 74b further has pin 132b connected to the electromagnet voltage supply 23.

A fresh, petroleum-based lubricating oil is primarily composed of hydrocarbon molecules with no net electrical charge and which are weakly polar or have a non-polar charge distribution. Fresh mineral oils can be characterized as having a very high electrical resistance and a relatively low dielectric constant (permittivity). These electrical properties change as the oil degrades and becomes contaminated. Specifically, increases in insoluble content, the presence of moisture and acids, or the presence of conductive metallic debris will increase the dielectric constant of an oil, or reduce its resistance, or both.

A combined measure of permittivity and resistivity can be made by measuring the AC impedance or effective capacitance (rate of charge over applied potential) across two plates separated by a quantity of oil. An approximate model for the system is an ideal capacitor influenced primarily by permitivity and a parallel resistance primarily influenced by ionic conduction. Charge mobility not involving conductive particles in a dielectric fluid involves mechanical motion of charged or dipole particles in the fluid. Therefore, system impedance is tied to the parameters which describe the hydrodynamics of particles moving in a fluid. These parameters include the temperature-dependent oil viscosity, the applied (electrical) forces, particle size, and particle shape. As might be expected, increasing molecular size and/or increasing viscosity damps particle response to electrical force, resulting in a decrease in the frequency at which the maximum effective capacitance is achieved. Consequently, simple readings of absolute instantaneous permittivity and loss performed with a conventional dielectrictrometer will provide a limited amount of information about the bulk oil chemistry.

The dielectric constant of a material is a dimensionless measure of how effectively that material shields an electric field. The dielectric constant for mineral oils falls in the range of 2.0 to 2.3. The dielectric constant for water is about 75. Phosphate ester synthetic oil has a dielectric constant of approximately 6.9. There are many factors affecting dielectric constant (i.e., how effectively that material shields an electric field): elemental composition, molecular make-up, entrained substances, etc. Those skilled in the art will know that a primary factor influencing dielectric constant is the proportion of elemental oxygen contained in the substance. This is one explanation for the range of values stated above for mineral oil (very low dielectric and very low oxygen content), phosphate ester (modest dielectric constant and approximately 17% oxygen), and water (very high dielectric constant and >90% oxygen).

The dielectric constant of an oil is affected by both the base stock (oil type; mineral or synthetic) but also by the additives to the base stock. As with the base stock, the dielectric constant contribution from the additive will be related to numerous factors including oxygen content, polar nature of molecules, acidity, and molecular structure (organic alcohols, acids, and esters).

Another important factor for base stock and for additives is the affect of temperature on dielectric constant. Most materials tend to show decreasing dielectric constant with increasing temperature. At the same time, increasing temperature can cause increased mobility for polar species (water) and ions in the oil plus additive.

All of these plus other factors combine to create the effects observed with respect to the inventions' ability to measure water in solution (dissolved), in emulsion (dispersed), and free water, and its ability to classify the type of lubricant by base stock and by gross additive concentration.

Additives are commonly formulated with lubricating oils and hydraulic power fluids to bring dispersant, emulsification and a variety of other enhancements to the base stock. The percentage of additive in a lubricant may be estimated from the total ppm of additive elements including zinc, calcium, magnesium, phosphorus, potassium, barium and sometimes, sodium. Considering that these elements are active parts of molecules, one might assume that the total additive content is 6 times the total for these elements. For example, a hydraulic oil with 1000 ppm of additive elements is likely to contain a total of about 6000 ppm or 0.6% additives. Table I displays typical ranges for elemental compositions of additive for various lubricant types.

Dispersant additives are used to prevent coalescing or agglomeration of soot, water, glycol or other such immiscible contaminants. Emulsifiers go beyond dispersion to combine water with the oil in an emulsion. The state or form that water will be drawn into when mixed with oil is highly dependent on the additive formulation. Accordingly, this additive formulation must be considered when using the present invention to measure water content with lubricants and hydraulic fluids.

Figure 6:
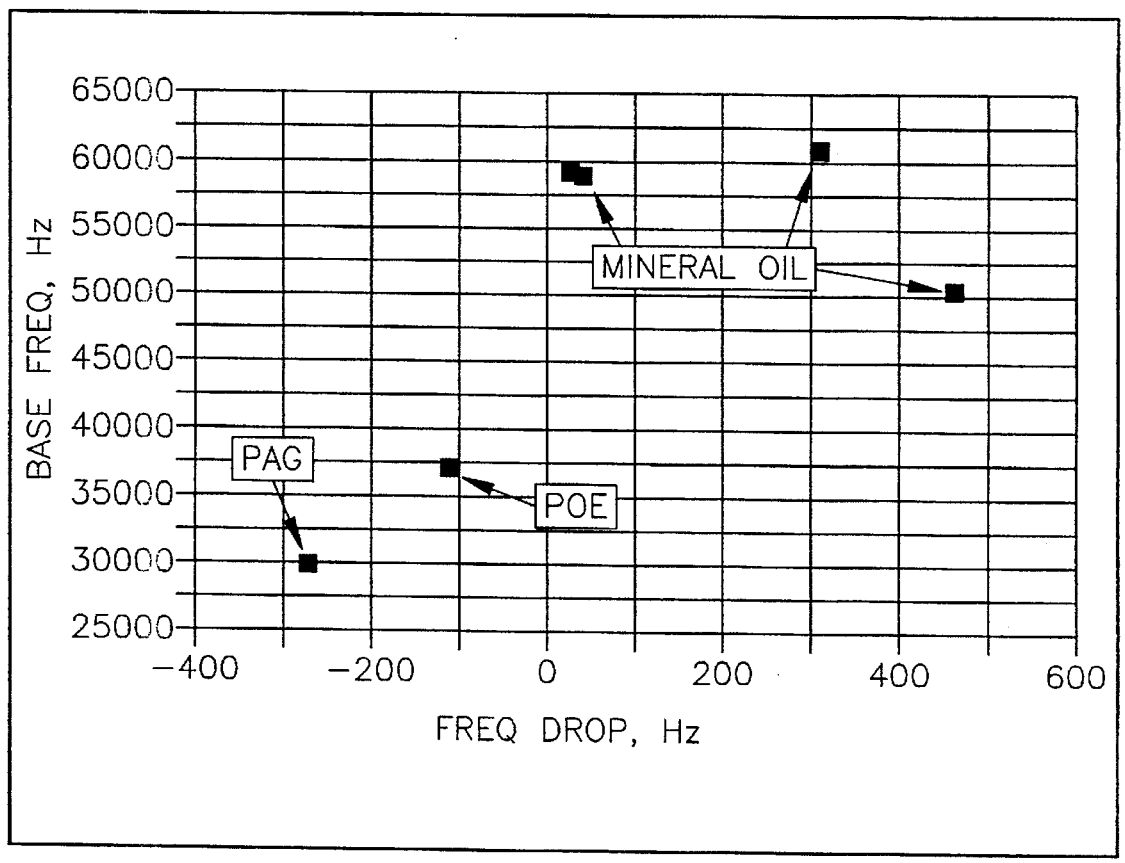
FIG. 6 is a graph of base frequency vs frequency drop due to a temperature rise for several different types of oil.
Figure 7:
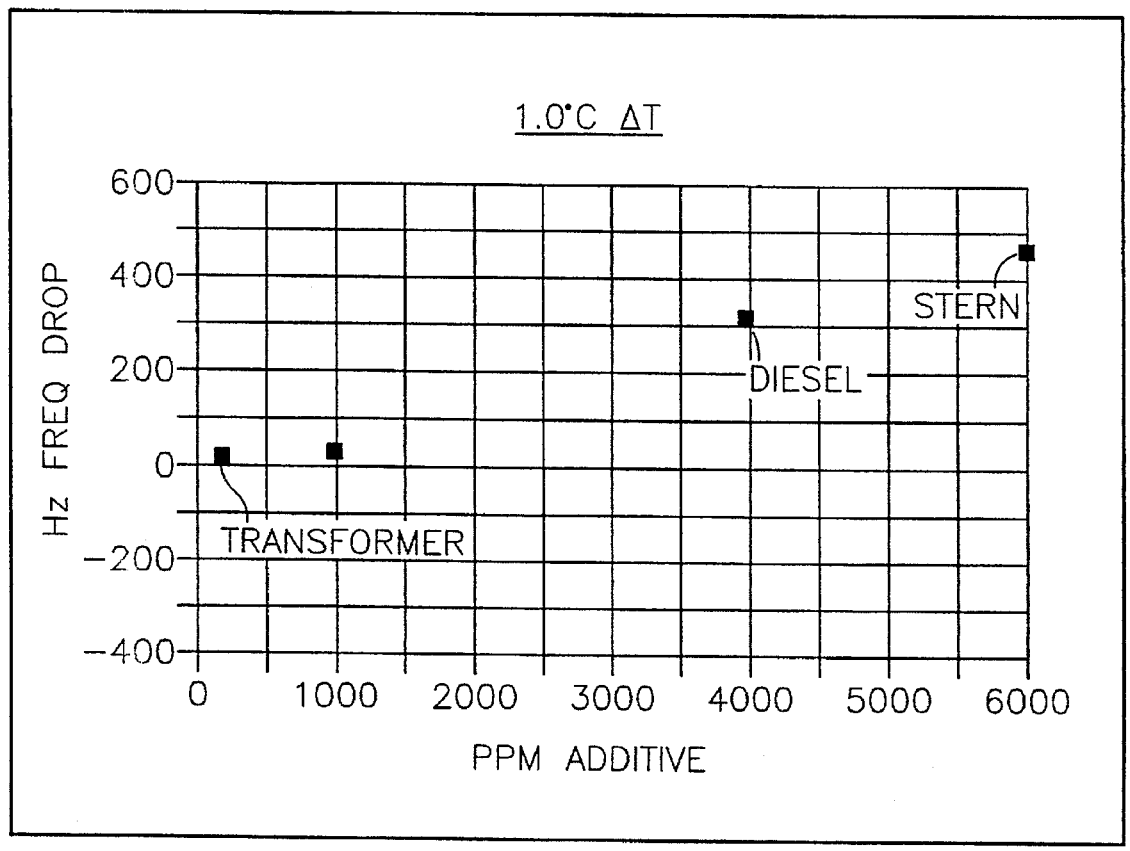
FIG. 7 is a graph of frequency drop due to a temperature rise vs additive quantity for several different mineral oils.

The interrelationships between dielectric constant, additive content and temperature change respective to specific lubricants are shown graphically by FIGS. 6 and 7. The graph of FIG. 6 reports data derived from three mineral oil based lubricants and two synthetic lubricants. The three mineral oil lubricants are distinguished by relative quantities of combined additives. Reported along the FIG. 6 graph ordinate (Y-axis) is the base frequency of the capacitor circuit including a sample of the lubricants as previously described. In this context, the "base frequency" is the natural frequency of the capacitor/oscillator system at the beginning of a 1.0° C. temperature rise. The abscissa (X-axis) of FIG. 6 reports the respective natural frequency changes between the "base" or starting frequency and the system natural frequency at the end of the 1.0° C. temperature increase.

FIG. 7 graphically reports the relationships of four mineral based oils between additive content along the abscissa and the natural frequency decline over the 1.0° C. temperature rise of the oil test samples. Here we see that a highly modified stern oil having 6000 ppm additive demonstrates a 450 Hz natural frequency drop over a temperature rise of 1.0° C. However, a transformer oil having only about 200 ppm additive loses only about 10 Hz over the same 1.0° C. temperature rise.

TABLE I

|  | ADDITIVE ELEMENTS | RANGES |
| --- | --- | --- |
| Automotive | Magnesium | 50–400 ppm |
|  | Sodium | 0–200 ppm |
|  | Barium | 0–150 ppm |
|  | Phosphorous | 700–1300 ppm |
|  | Calcium | 400–2000 ppm |
|  | Zinc | 800–1400 ppm |
|  | Total | ≈4000 ppm |
| Industrial Gear Oil | Barium | 0–25 ppm |
|  | Phosphorous | 300–750 ppm |
|  | Calcium | 5–50 ppm |
|  | Zinc | 500–1000 ppm |
|  | Total | ≈1500 ppm |
| E P Additive Gear Oil | Sodium | 75–500 ppm |
|  | Boron | 998 ppm |
|  | Phosphorus | 175–425 ppm |
|  | Calcium | 10–150 ppm |
|  | Zinc | 300–550 ppm |
|  | Total | ≈1500 ppm |
| Hydraulic Oils | Barium | 0–200 ppm |
|  | Phosphorus | 225–325 ppm |
|  | Calcium | 25–150 ppm |
|  | Zinc | 350–500 ppm |
|  | Total | ≈1000 ppm |
| Compressor Oils | Barium | 0–200 ppm |
|  | Phosphorus | 0–35 ppm |
|  | Calcium | 0–35 ppm |
|  | Zinc | 0–50 ppm |
|  | Total | ≈200 ppm |

Pursuant to the invention, mineral oil lubricants were classified in four categories with respect to mixed or blended performance enhancing additives: heavy, moderate, light and none. A typical example of a heavy additive oil would be found in the crankcase of an industrial diesel engine. Industrial pump oil is fortified with a moderate additive concentration. Hydraulic or power transmission oil includes a light charge of additives and transformer oil is free of additives. These subjective classifications are objectively defined in terms of a raw data count or natural frequency differential over a standard temperature rise of about 1.0° C.

As an illustration, a container volume of lightly supplemented but uncontaminated new turbine oil is placed in wet contact with the sensor 16 and the electronic and magnet power circuits energized for a standard test period of 500 seconds, for example. Heat originating from the electromagnet 20 beneath the sensor 16 rises into the oil sample over the standard test period to raise the sample temperature about 1.0° C. This rise in temperature increases the test oil dielectric constant value which, consequently, reduces the natural frequency of the oscillator circuit 26. Hence, the frequency of multivibrator 40 declines over the standard test period by 30 to 70 Hz. This natural frequency decline is to be understood as a characteristic of the clean, dry, uncontaminated oil.

To quantify the effects of subsequently introduced contaminants, it will be necessary to isolate the characteristics of uncontaminated oil from the measured parameters of contaminated oil which will necessarily incorporate the uncontaminated oil characteristics. Hence, it is essential that an uncontaminated reference oil be essentially anhydrous when analyzed for inherent, thermal response characteristics.

To assure the substantial absence of water in a reference oil test sample, affirmative water removal procedures are recommended. Among the candidate drying procedures are: heating; centrifugal separation; vacuum dehydration; and, drying agents. Drying agents are preferred as most reliable and practical for reducing water content below a predetermined threshold, less than 0.01 ppm, for example. Two suitable drying agents include desiccants and molecular sieves. A preferred desiccant is Drierite, a proprietary anhydrous calcium sulfate product of the W. A. Hammond Drierite Co.; Xenia, Ohio. Molecular sieves can remove water from oil down to 0.001 ppm. Drierite can remove water down to 0.005 ppm but changes colors when water saturated, thereby providing an immediate visual indication of water presence.

Although drying agents are not usually practical with a working lubricant due to the abrasive nature of the solid contaminant, this consequence has no bearing on the present invention procedures for calibrating the inherent electrical and affinity characteristics of an oil type.

In some cases, advantages may be found for using drying agents in samples of contaminated oil, also. Without water, better estimates of the presence and amounts of oxidation/degradation products or contaminants may be possible.

For use and handling convenience, drying agents may be secured to or suspended within the test sample container 10.

Figure 9:
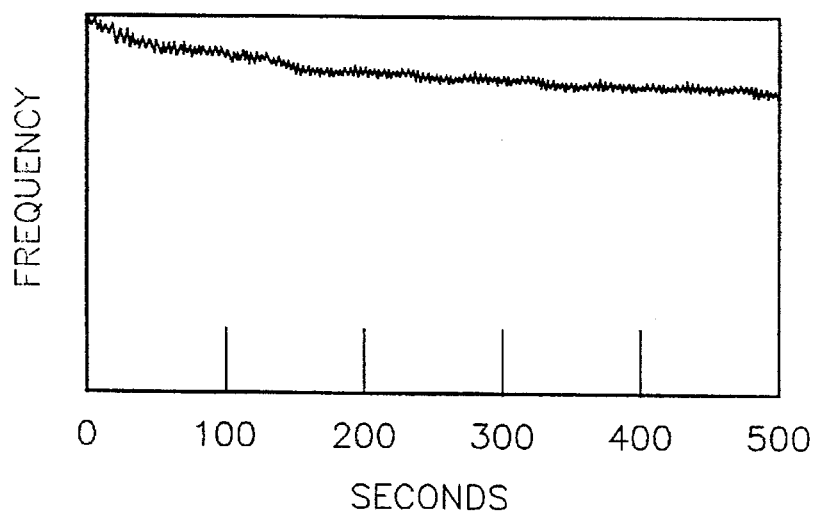
FIG. 9 is a graph of frequency vs time data taken by the invention from uncontaminated lubricating oil.

The above relationships are shown by FIG. 9 which plots the multivibrator 40 frequency over a 500 second test period as a percentage of the starting natural frequency of the oscillator. Wetting the sensor 16 is an uncontaminated turbine oil having a light additive modification. It will be observed that over the 500 second test period the multivibrator 40 frequency declined by 0.05% or 30 Hz.

The data of Table II reports an experimentally developed correlation between lubricant additive classifications and respective water affinity rate characteristics. Column A reports characteristic ranges of natural frequency change respective to a lubricant class over a standard, 500 second heating period during which the test sample rises about 1.0° C. Most natural petroleum based lubricants experience a natural frequency decline over the test period. Synthetic lubricants such as polyalkylene glycol and polyol ester exhibit an increased natural frequency.

TABLE II

| Lub. Class. | Nat. Freq. Change, $\Delta f$, Hz | | Combined Moisture, % $H_2O/\Delta f$ | |
|---|---|---|---|---|
| | A | | B | C |
| | from | to | Solution | Free/Emulsified |
| Synth:PAG 1 | +150 | +1000 | $40 \times 10^{-5}$ | $40 \times 10^{-5}$ |
| Synth:POE 2 | +30 | +151 | $28.6 \times 10^{-5}$ | $28.6 \times 10^{-5}$ |
| Transformer | −25 | +29 | $1.26 \times 10^{-6}$ | $1.26 \times 10^{-6}$ |
| Turbine | −26 | −60 | $2.0 \times 10^{-5}$ | $4.0 \times 10^{-5}$ |
| Indust. | −61 | −150 | $25 \times 10^{-5}$ | $25 \times 10^{-5}$ |
| Diesel | −150 | −350 | $50 \times 10^{-5}$ | $50 \times 10^{-5}$ |
| Stern | −351 | −1000 | $18 \times 10^{-4}$ | $9.0 \times 10^{-4}$ |

1 Polyalkylene glycol
2 Polyol Ester

Figure 8:
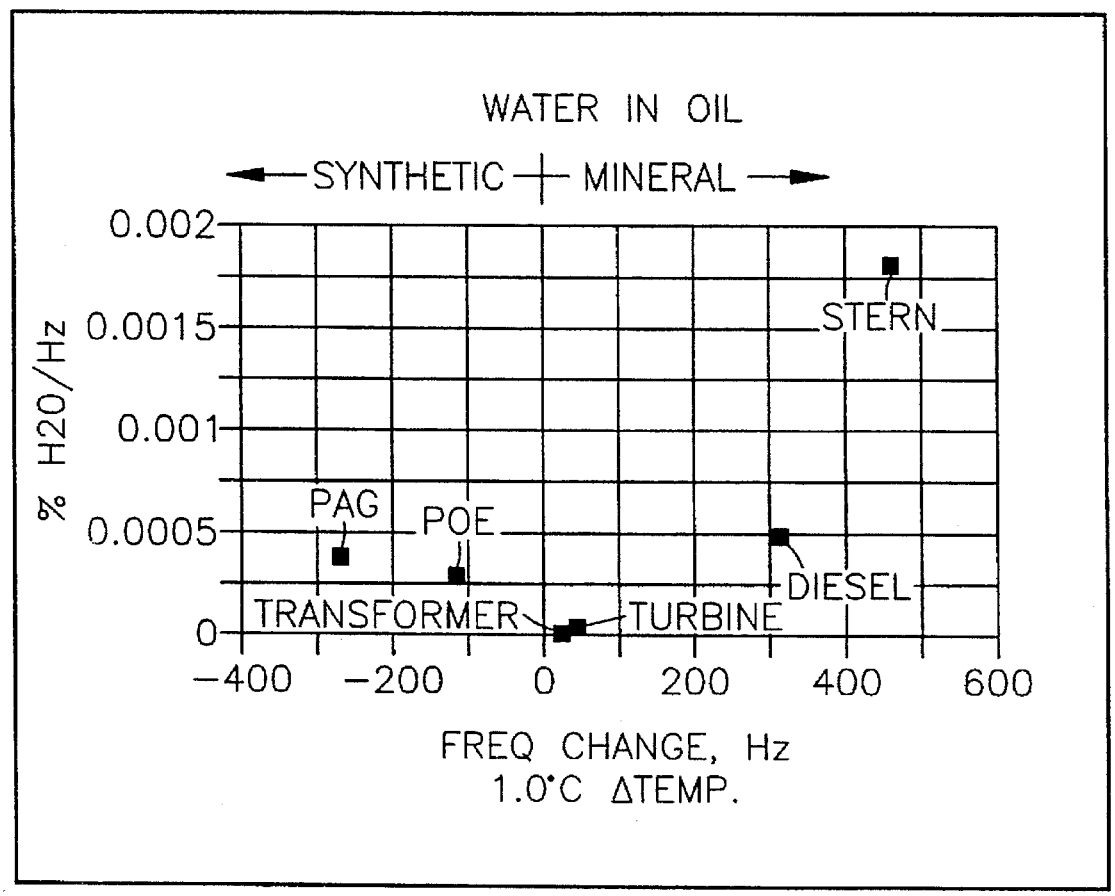
FIG. 8 is a graph of water affinity rate per unit of frequency vs frequency change due to a temperature rise in several differing types of oil.

The data of Column B, Table II, correlates the rate relationships between the change of natural frequency and percentage of water content per unit of frequency change respective to the same lubricant classifications. Column C correlates the rate relationship between the change of natural frequency attributed to free and emulsified water in the oil and the percentage of free water in the lubricant system. This data is graphically reported by FIG. 8 which charts water affinity rate, % $H_2O$/Hz, along the graph ordinate and corresponding natural frequency changes from the base frequency over an approximately 1.0° C. temperature rise along the graph abscissa. Each class of lubricant has a different affinity constant for water due to its base oil and additive composition. These constants, when multiplied by the measured natural frequency change, yield the water content of the test oil in each of the three physical states: solution, emulsified and free.

Figure 10:
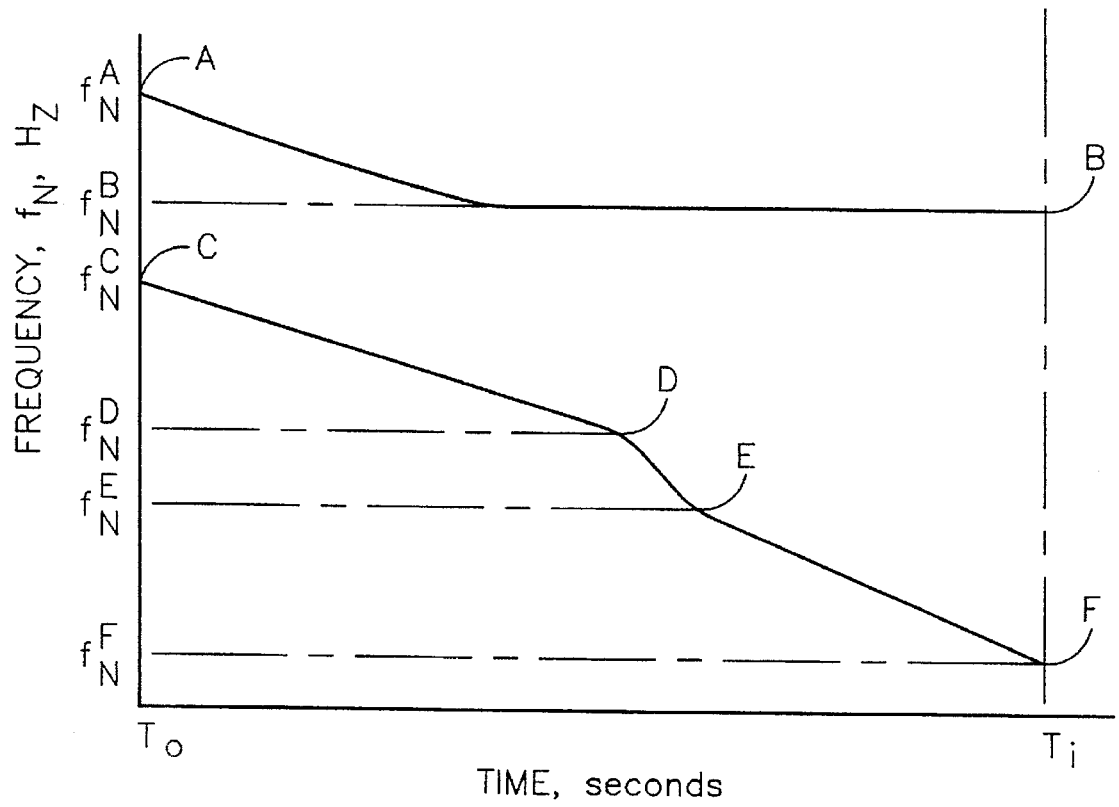
FIG. 10 is a graph of frequency vs time data taken by the invention from an idealized uncontaminated lubricating oil and the same oil after significant use and wear.

With respect to FIG. 10 and the data of Table II, the curves shown are idealized to illustrate the principles underlying the invention. Curve A-B represents a typical, uncontaminated sample of moderate additive oil, wherein the dielectric constant rises modestly due to equipment heating over the standard test interval $T_i$. The natural frequency decline from the starting frequency $f_n^A$ at the starting time of $T_o$, is a signatory characteristic of the oil and is tabulated within Column A of Table II.

Curve C-F represents the same moderate additive oil as A-B but contaminated by the presence of water in several forms. The natural frequency differential $f_n^A - f_n^C$ at the test starting time $T_o$ represents dissolved water that has combined, for example, with metal salt additives as a hydrate. The percentage of water rate of that solution combination as a function of the frequency differential is tabulated within Column B of Table II.

The overall frequency decline of curve C-E is simplistically represented in three segments. To wit, C-D, D-E and E-F. The substantially linear segments of the curve i.e., C-D and E-F are stimulated by a gravity settled accumulation of emulsified water molecules in the sensory proximity of the sensing element 16 surface. Water in this form is characterized as "dispersed" or emulsified and the percentage rate of that dispersion as a function of the frequency differential is also tabulated by the Column B of Table II. In the FIG. 10 example, the total percentage of water dispersed within the oil system is the sum of the frequency differential segments.

$$\Delta f(\text{dispersed}) = (f_n^C - f_n^D) + (f_n^E - f_n^F) \qquad \text{Formula 3}$$

The D-E segment of curve C-F is an anomaly by the definition of a slope that is five times greater than the median slope of curve C-F. Such anomaly events are attributed to the settlement of free water droplets upon the sensing element 16 surface to stimulate a capacitance discharge surge. The percentage of water in the system is determined as a function of the frequency differential $f_n^D - f_n^E$ and the data tabulated by Column C of Table II.

Collectively, therefore, the total water in the oil, as a percentage of weight value, is the sum of dissolved water, dispersed water and free water.

Depending on the degree of oil contamination, the curve C-F may be considerably more complex than represented by FIG. 10. In such cases, it is useful to characterize the curve in several segments of time. For example, the total time interval, $T_i$, may be analyzed as five equal segments of time. For each segment, the curve slope is determined linearly between the entrance and exit coordinates. The median is selected as that slope remaining after an interactive exclusion of extreme pairs. Having determined a median, extreme slopes are compared to identify those that may constitute free water anomalies by being five times or more greater than the median.

Table III presents a data base for six lubricant classes and thirty test runs among the six classes. The respective lubricant classes are listed in column A of Table III to include polyol ester, a synthetic lubricant, poly alkylene glycol, another synthetic lubricant, diesel crankcase lubricant, turbine lubricant, electric transformer dielectric oil and stern oil for sealing water immersed rotating shafts.

Under column B of Table III is listed the actual percentage quantity of total water present in the test sample in all forms; the sum of solution, emulsion and free water in the test sample presence. Column C lists the total quantity of water calculated by the present invention procedure to be present in the respective test sample.

Column D of Table III lists the initially measured natural frequency of the respective test sample and column E lists the natural frequency of the sensor system at the 500 second conclusion of a respective test. The units of columns D and E are Hertz, Hz.

Column F lists the frequency differential, in Hz, representative of a free water anomaly when present.

Column G lists the frequency differential, in Hz, between the initial natural frequency test values respective to an uncontaminated reference sample of oil having no water and a contaminated oil sample.

TABLE III

| TEST | LUBRICANT A | % H₂O Actual B | % H₂O Calc C | NATURAL FREQ. f, Hz Start D | NATURAL FREQ. f, Hz End E | Δf, Hz Step F | Δf, Hz Offset G | Δf, Hz Drop H | RATE % H₂O/Δf Solution I | RATE % H₂O/Δf Free/Emul J |
|---|---|---|---|---|---|---|---|---|---|---|
| 1 | POE (1) | 0 | 0 | 37240 | 37350 | 0 | 0 | −110 | $28.6 \times 10^{-5}$ | $28.6 \times 10^{-5}$ |
| 2 | | 0.04 | 0 | 37220 | 37240 | 0 | −20 | −20 | $28.6 \times 10^{-5}$ | $28.6 \times 10^{-5}$ |
| 3 | | 0.08 | 0 | 37200 | 37170 | 0 | −40 | 30 | $28.6 \times 10^{-5}$ | $28.6 \times 10^{-5}$ |
| 4 | | 0.16 | 0.1 | 37010 | 36880 | 0 | −230 | 130 | $28.6 \times 10^{-5}$ | $28.6 \times 10^{-5}$ |
| 5 | | 0.32 | 0.3 | 36550 | 35850 | 140 | −690 | 700 | $28.6 \times 10^{-5}$ | $28.6 \times 10^{-5}$ |
| 6 | | 0.64 | 0.6 | 36110 | 34990 | 0 | −1130 | 1120 | $28.6 \times 10^{-5}$ | $28.6 \times 10^{-5}$ |
| 7 | | 1.28 | 1.2 | 35930 | 33130 | 0 | −1310 | 2800 | $28.6 \times 10^{-5}$ | $28.6 \times 10^{-5}$ |
| 8 | PAG (2) | 0 | 0 | 29920 | 30190 | 0 | 0 | −270 | $40.0 \times 10^{-5}$ | $40.0 \times 10^{-5}$ |
| 9 | | 0.04 | 0 | 29800 | 30070 | 0 | −120 | −270 | $40.0 \times 10^{-5}$ | $40.0 \times 10^{-5}$ |
| 10 | | 0.08 | 0 | 29710 | 29990 | 0 | −210 | −280 | $40.0 \times 10^{-5}$ | $40.0 \times 10^{-5}$ |
| 11 | | 0.16 | 0.1 | 29540 | 29810 | 0 | −380 | −270 | $40.0 \times 10^{-5}$ | $40.0 \times 10^{-5}$ |
| 12 | | 0.32 | 0.2 | 29160 | 29410 | 0 | −760 | −250 | $40.0 \times 10^{-5}$ | $40.0 \times 10^{-5}$ |
| 13 | | 0.64 | 0.4 | 28520 | 28780 | 0 | −1400 | −260 | $40.0 \times 10^{-5}$ | $40.0 \times 10^{-5}$ |
| 14 | | 1.28 | 0.8 | 27070 | 27180 | 0 | −2850 | −110 | $40.0 \times 10^{-5}$ | $40.0 \times 10^{-5}$ |
| 15 | DIESEL | 0 | 0 | 60960 | 60650 | 0 | 0 | 310 | $50.0 \times 10^{-5}$ | $50.0 \times 10^{-5}$ |
| 16 | | 0.1 | 0.05 | 60680 | 60300 | 0 | −280 | 380 | $50.0 \times 10^{-5}$ | $50.0 \times 10^{-5}$ |
| 17 | | 0.5 | 0.41 | 60600 | 59530 | 0 | −360 | 1070 | $50.0 \times 10^{-5}$ | $50.0 \times 10^{-5}$ |
| 18 | | 0.75 | 0.79 | 60050 | 58480 | 0 | −910 | 1570 | $50.0 \times 10^{-5}$ | $50.0 \times 10^{-5}$ |
| 19 | | 1 | 0.89 | 60430 | 58690 | 0 | −530 | 1740 | $50.0 \times 10^{-5}$ | $50.0 \times 10^{-5}$ |
| 20 | TURBINE | 0 | 0 | 59530 | 59500 | 0 | 0 | 30 | $2.0 \times 10^{-5}$ | $4.0 \times 10^{-5}$ |
| 21 | | 0.03 | 0.01 | 59240 | 58700 | 0 | −290 | 540 | $2.0 \times 10^{-5}$ | $4.0 \times 10^{-5}$ |
| 22 | | 0.13 | 0.13 | 59520 | 56110 | 0 | −10 | 3410 | $2.0 \times 10^{-5}$ | $4.0 \times 10^{-5}$ |
| 24 | TRANSF | 0 | 0 | 59720 | 59700 | 0 | 0 | 20 | $12.6 \times 10^{-7}$ | $13.0 \times 10^{-7}$ |
| 25 | | 0.005 | 0.1 | 59690 | 55740 | 0 | −30 | 3950 | $12.6 \times 10^{-7}$ | $13.0 \times 10^{-7}$ |
| 26 | STERN | 0 | 0 | 50290 | 49830 | 0 | 0 | 460 | $18.0 \times 10^{-4}$ | $9.0 \times 10^{-4}$ |
| 27 | | 2.3 | 3 | 49090 | 47110 | 0 | −1200 | 1980 | $18.0 \times 10^{-4}$ | $9.0 \times 10^{-4}$ |
| 28 | | 5.7 | 5.3 | 47970 | 45510 | 0 | −2320 | 2460 | $18.0 \times 10^{-4}$ | $9.0 \times 10^{-4}$ |
| 29 | | 11 | 9.3 | 45400 | 42650 | 0 | −4890 | 2750 | $18.0 \times 10^{-4}$ | $9.0 \times 10^{-4}$ |
| 30 | | 16 | 12.7 | 43180 | 39960 | 0 | −7110 | 3220 | $18.0 \times 10^{-4}$ | $9.0 \times 10^{-4}$ |

| TEST | ppm Additive K | H₂O, % Solution L | H₂O, % Emul M | H₂O, % Free N | H₂O, % Sum O | Error H₂O, % Diff P |
|---|---|---|---|---|---|---|
| 1 | | 0 | 0 | 0 | 0 | 0 |
| 2 | | 0.00572 | 0.02574 | 0 | 0.03146 | −0.00854 |
| 3 | | 0.01144 | 0.04004 | 0 | 0.05148 | −0.02852 |
| 4 | | 0.06578 | 0.06864 | 0 | 0.13442 | −0.02558 |
| 5 | | 0.19734 | 0.19162 | 0.04004 | 0.429 | 0.109 |
| 6 | | 0.32318 | 0.35178 | 0 | 0.67496 | 0.03496 |
| 7 | | 0.37466 | 0.83226 | 0 | 1.20692 | −0.07308 |
| 8 | | 0 | 0 | 0 | 0 | 0 |
| 9 | | 0.048 | 0 | 0 | 0.048 | 0.008 |
| 10 | | 0.084 | −0.004 | 0 | 0.08 | 0 |
| 11 | | 0.152 | 0 | 0 | 0.152 | −0.008 |
| 12 | | 0.304 | 0.008 | 0 | 0.312 | −0.008 |
| 13 | | 0.56 | 0.004 | 0 | 0.564 | −0.076 |
| 14 | | 1.14 | 0.064 | 0 | 1.204 | −0.076 |
| 15 | 4000 | 0 | 0 | 0 | 0 | 0 |
| 16 | 4000 | 0.14 | 0.035 | 0 | 0.175 | 0.075 |
| 17 | 4000 | 0.18 | 0.38 | 0 | 0.56 | 0.06 |
| 18 | 4000 | 0.455 | 0.63 | 0 | 1.085 | 0.335 |
| 19 | 4000 | 0.265 | 0.715 | 0 | 0.98 | −0.02 |
| 20 | 1000 | 0 | 0 | 0 | 0 | 0 |
| 21 | 1000 | 0.0058 | 0.0204 | 0 | 0.0262 | −0.0038 |
| 22 | 1000 | 0.0002 | 0.1352 | 0 | 0.1354 | 0.0054 |
| 24 | 200 | 0 | 0 | 0 | 0 | 0 |
| 25 | 200 | $3.8 \times 10^{-5}$ | 0.004952 | 0 | 0.00499 | $-1.0 \times 10^{-5}$ |
| 26 | 6000 | 0 | 0 | 0 | 0 | 0 |
| 27 | 6000 | 2.16 | 1.368 | 0 | 3.528 | 1.228 |
| 28 | 6000 | 4.176 | 1.8 | 0 | 5.976 | 0.276 |
| 29 | 6000 | 8.802 | 2.061 | 0 | 10.863 | 0.137 |
| 30 | 6000 | 12.798 | 2.484 | 0 | 15.282 | −0.718 |

(1) polyol ester
(2) polyalkylene glycol

Column H lists the frequency change differential, in Hz, between the initial natural frequency test values respective to a test sample and the corresponding values after a 500 second test interval that heats the test sample by about 1.0°

C. The data of this column is derived as the difference between columns D and E and corresponds to the graph of FIG. 6.

Columns I and J of Table III list the empirically developed rate of water percentage per frequency differential applied to calculate the total water quantity present in a sample from the measurable values. The column I rate values are applicable to dissolved water determination criteria whereas the column J values apply to the determination of emulsified and free water.

Column K lists the additive concentration content for various tested lubricants in units of parts per million as a distinctive characteristic of the lubricant.

Column L of Table III lists the calculated percentage of water present in the respective test sample in solution form with the lubricant or its additives. Column M lists the calculated percentage of water present in a respective test sample in the form of an emulsion. Column N lists the calculated percentage of water present in the samples in free droplet form. Column O lists the total percentage quantity of water calculated to be present in the respective samples determined as a summation of columns L, M and N. Column P lists the respective differences between the actual water quantities known to be present in the several examples and the quantities calculated by the present invention process to be present.

EXAMPLE I

To demonstrate the procedure of the invention, reference is first given to the Table III data respective to Test No. 1. This test is among a group of seven tested examples of the synthetic lubricant polyalkylene glycol (POE). Test 1 was of an uncontaminated sample of POE which experienced a natural frequency rise from 37,240 Hz (col. D) to 37,350 Hz (col. E) at the end of the 500 second test interval. The 110 Hz rising frequency change (col. H) is arbitrarily assigned a negative sign quality since petroleum based lubricants exhibit a declining natural frequency which is assigned a positive value. By experimentation, water, as a percentage of weight, has been found to combine or mix with POE at the rate of $28.6 \times 10^{-5}\%$ water per Hertz difference over the 500 second test interval in all three designated states of solution (col. I), emulsion (col. J) and free droplets (col. J).

The values of a 110 Hz frequency change (col. H) over the 500 second interval and a $28.6 \times 10^{-5}\%$ $H_2O/\Delta f$ contamination rate (cols. I&J) for samples of POE are material Property characteristics of POE. Consequently, without actual knowledge of a lubricant identity, measurement of a $-110$ Hz dry test sample natural frequency change over standard 500 second (or any other corresponding standard) test interval reveals the unknown sample to be POE having a $28.6 \times 10^{-5}\%$ $H^2O/\Delta f$ water affinity rate in all categories.

EXAMPLE II

Figure 11:
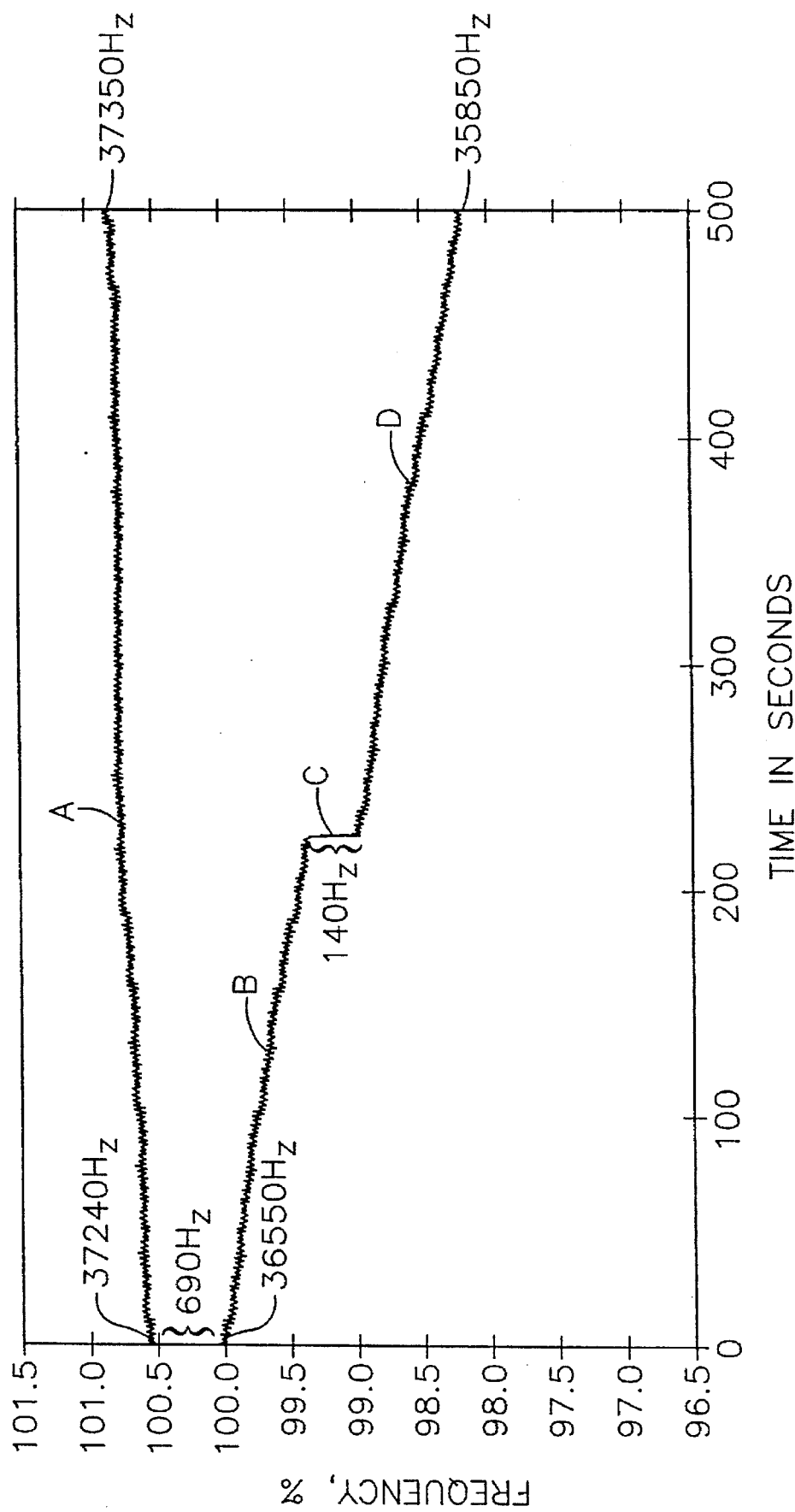
FIG. 11 is a graph of frequency vs time data taken by the invention from the synthetic lubricant polyol ester having approximately 0.32% water entrained therewith.

Applying the foregoing information to the contaminated sample of Test No. 5, reference is given to the graph of FIG. 11. Plot line A of the graph represents the data sequence of the uncontaminated sample of POE from Test No. 1. Test No. 5 starts with an initial natural frequency of 36,550 Hz (col. D), shown on the FIG. 11 graph as 100% along the frequency ordinate. This initial natural frequency difference between the uncontaminated sample of 690 Hz is listed in the offset frequency difference column G of Table III and, by the water affinity rate of column I, is related to the percentage quantity of water that is in solution combination with the lubricant.

Expansively:

$$690 Hz \times 28.6 \times 10^{-5}\% \ H_2O/\Delta f = 0.19734\% \ H2O (col. L)$$

Referring again to FIG. 11, from the initial natural frequency of 36,550 Hz the natural frequency of the contaminated POE sample declines at a substantially linear rate as the test interval progresses over the plot increment B until about 220 seconds into the interval when the sample natural frequency plummets abruptly by 140 Hz (col. F) along plot increment C. This abrupt change in the natural frequency decline signals a sudden short contact across the capacitor grid conductors 32A and 32B by a droplet of free water. The percentage quantity of this free water droplet is related to the abrupt frequency change of 140 Hz and the free water affinity rate of $28.6 \times 10^{-5}\%$ $H_2O/Hz$ (col J).

Expansively:

$$140 \ Hz \times 28.6 \times 10^{-5}\% \ H_2O/Hz = 0.4004\% \ H_2O \ (col. \ H)$$

Following the free water induced anomaly C, the Test No. 5 progression resumes a substantially linear rate of natural frequency decline along plot increment D until the 500 second conclusion of the standard test interval. At conclusion, the natural frequency of the contaminated sample of Test No. 5 has a natural frequency of 35,850 Hz (col. E). This represents a gross decline of 700 Hz (col. H). However, 140 Hz of this decline was due to the free water anomaly. Furthermore, the uncontaminated characteristic of this oil is a natural frequency increase of 110 Hz by the end of the 500 second test interval. Accordingly, $$700 \ Hz + 110 \ Hz - 140 \ Hz = 670 \ Hz$$

This 670 Hz decline in natural frequency is attributable to emulsified water. The quantity of this emulsified water in the contaminated sample is related by the affinity rate of $28.6 \times 10^{-5}\%$ $H_2O/Hz$ (col. J).

Expansively:

$$670 \ Hz \times 28.6 \times 10^{-5}\% \ H_2O/Hz = 0.19162\% (col \ M)$$

Having determined all three water contamination categories, the calculated data of columns L, M and N is added to conclude the total water present in the contaminated sample of Test No. 5 which was initially known to actually be 0.320% $H_2O$.

Expansively:

$$0.19734\% + 0.19162\% + 0.04004\% = 0.4290\% \ (col \ O)$$

The error, therefore, is:

$$0.4290\% - 0.320\% = 0.109\% \ (col \ P)$$

EXAMPLE III

In the next example of the present analytical procedure, Test No. 20 was conducted with an uncontaminated turbine oil having about 1000 ppm additive combined therewith. Data from Test No. 20 is graphically shown by FIG. 12 as plot A starting with an initial natural frequency of 59,530 Hz (col. D) and concluding after 500 seconds with a natural frequency of 59,500 Hz (col. E): a decline of 30 Hz (col. H).

EXAMPLE IV

Figure 12:
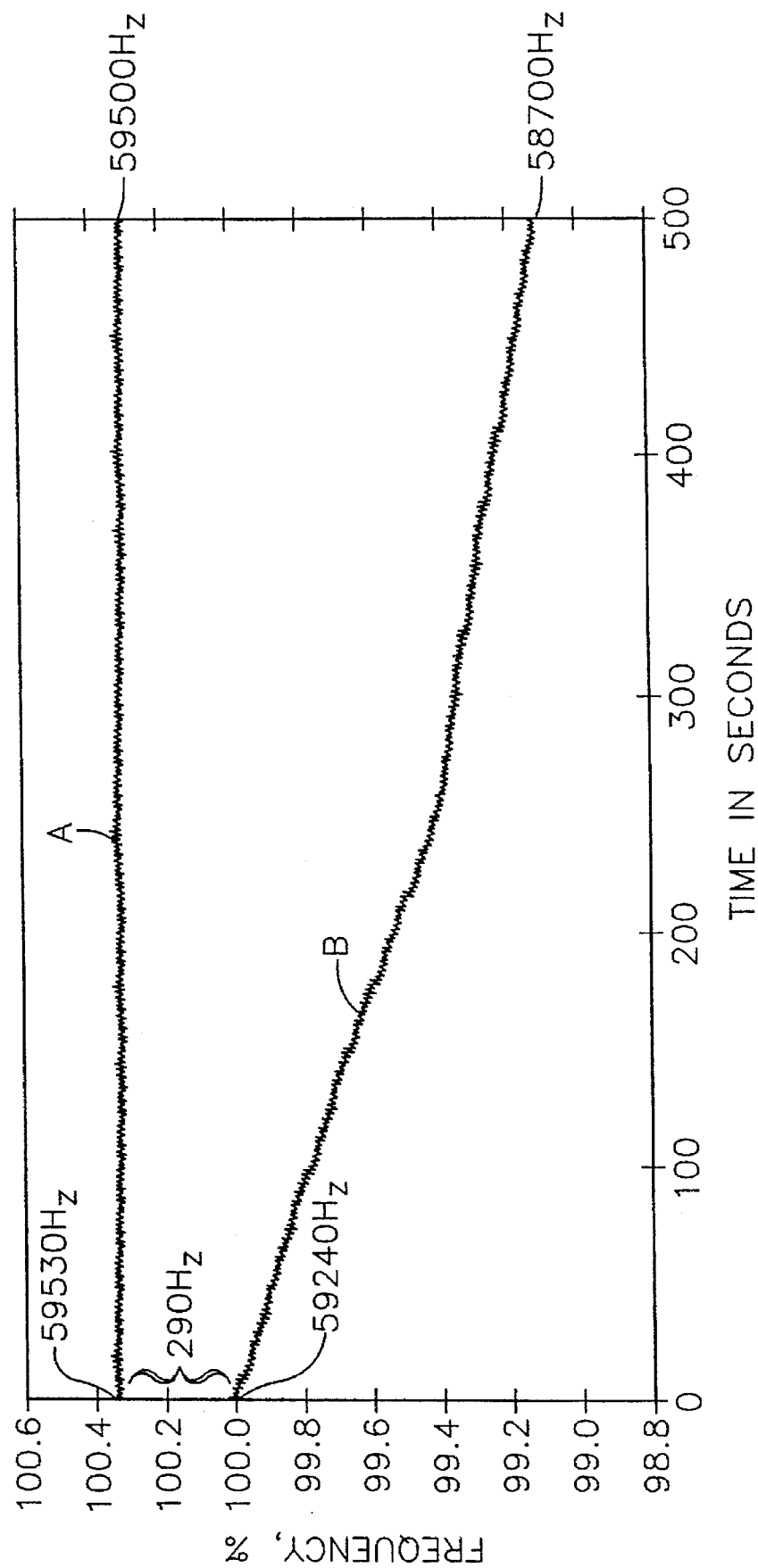
FIG. 12 is a graph of frequency vs time data taken by the invention from a light turbine oil having approximately 0.03% water entrained therewith.

The contaminated turbine oil sample of Test No. 21 is shown in the FIG. 12 graph as plot B starting at an Initial natural frequency of 59,240 Hz, 100% along the Frequency ordinate of FIG. 12 and finishing at the end of 500 seconds at 58,700 Hz. The frequency offset between the initial natural frequency of the uncontaminated turbine oil sample of plot A (Test No. 20) and the initial natural frequency of the contaminated turbine oil sample of plot B (Test No. 21) is 290 Hz (col.G). The water in solution affinity rate for this lubricant is $2.0 \times 10^{-5}\%$ $H_2O$/Hz (col. I). Combining, the initial frequency difference with the solution water affinity, 0.0058% water is present in solution with the additives of the Text No. 21 sample.

Expansively:

290 Hz×$2.0 \times 10^{-5}\%$ $H_2O$/Hz=0.0058% $H_2O$(col. L)

With further reference to FIG. 9, it will be noted that although plot B is not linear, the expotentiality of the plot is not great. Accordingly, the plot will considered as linear with an emulsified water affinity rate of $4.0 \times 10^{-5}\%$ $H_2O$/Hz (col. J). It will also be noted that the progression of plot B is substantially faired and continuous from start to finish thereby suggesting no free water anomalies. The gross natural frequency decline of the contaminated test sample from the initial natural frequency of 59,240 Hz to the final natural frequency of 58,700 Hz is 540 Hz. However, 30 Hz of this gross decline is attributable to the uncontaminated oil characteristic (Test No. 20, col. H). The net natural frequency decline of the Test No. 21 contaminated oil sample attributable to emulsified water is 510 Hz.

Expansively:

510 Hz×$4.0 \times 10^{-5}\%$ $H_2O$/Hz=0.0204% $H_2O$ (col. M)

Collectively, the total water present in the Test No. 21 turbine oil sample is:

|   | 0.0058% | Dissolved | $H_2O$ |
|---|---|---|---|
| + | 0.0204% | Emulsified | $H_2O$ |
|   | 0.0262% | Total | $H_2O$ |

EXAMPLE V

Figure 13:
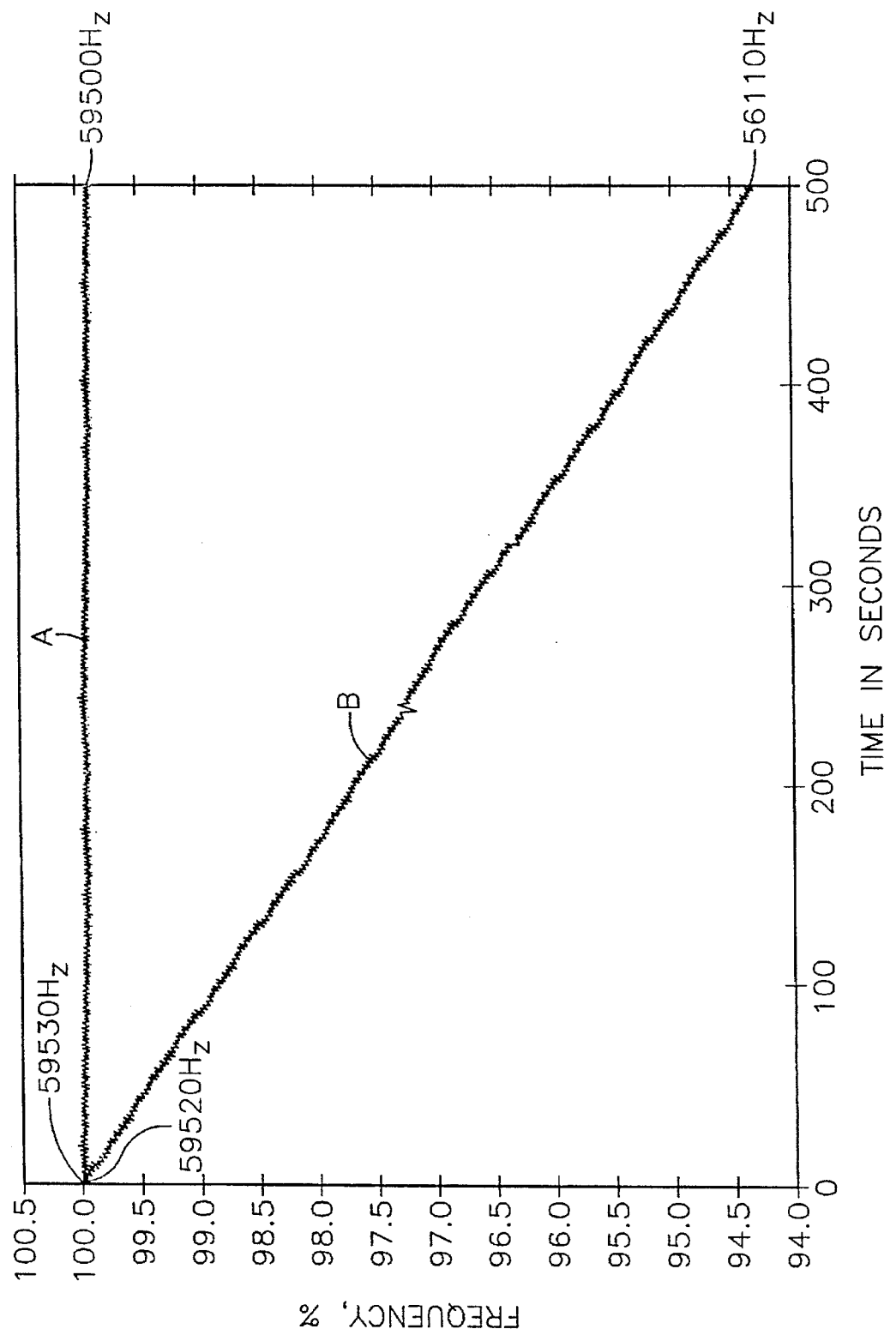
FIG. 13 is a graph of frequency vs time data taken by the invention from a light turbine oil having approximately 0.13% water entrained therewith.

Data plot A of FIG. 13 is another presentation of the Test No. 20 data whereas plot B illustrates the data of Test No. 22 which is known to have an actual water contamination content of 0.13%. The initial natural frequency of plot B is 59,520 Hz which is only 10 Hz less than the initial natural frequency of 59,530 Hz for uncontaminated turbine oil (Test No. 20). Applied to a water affinity rate of $2.0 \times 10^{-5}\%$ $H_2O$/Hz=0.0002% $H_2O$ it is found that 0.0002% $H_2O$ is combined in solution.

Expansively:

10 Hz×$2.0 \times 10^{-5}\%$ $H_2O$/Hz=0.0002% $H_2O$ dissolved

The final natural frequency of plot B is 56,110 Hz, 3410 Hz (col. H) less than the initial frequency of 59,520 Hz. Although the Test No. 22 plot B follows a substantially continuous linear decline over the 500 second test interval, an anomaly at about 250 seconds is noted in a spike. However, the spike is insufficient to displace the mean path of the plot and therefore will be ignored. The emulsion suspended water value will be the product of the net natural frequency decline and the $2.0 \times 10_{-5}\%$ $H_2O$/Hz emulsified water affinity rate. The net natural frequency decline is the gross decline corrected by the uncontaminated oil characteristic decline of 30 Hz. The net decline, therefore, is 3410 Hz−30 Hz=3380 Hz. The quantity of emulsified water is:

3380 Hz×$4.0 \times 10^{-5}\%$ $H_2O$/Hz=0.1352% $H_2O$ emulsified

Collectively, the total water present in the Test No. 22 sample is:

|   | 0.0002% | dissolved |
|---|---|---|
| + | 0.1352% | emulsified |
|   | 0.1354% | Total |

EXAMPLE VI

Tests 26–30 are of a highly modified lubricant called "stern" oil prepared predominantly for maritime applications. Referring to column K of Table III, this oil typically comprises 6000 ppm additive compounds. Consequently, the composition has an extremely high affinity for dissolved water as reflected by the rate of $18.0 \times 10^{-4}\%$ $H_2O$/Hz (col. I).

Figure 14:
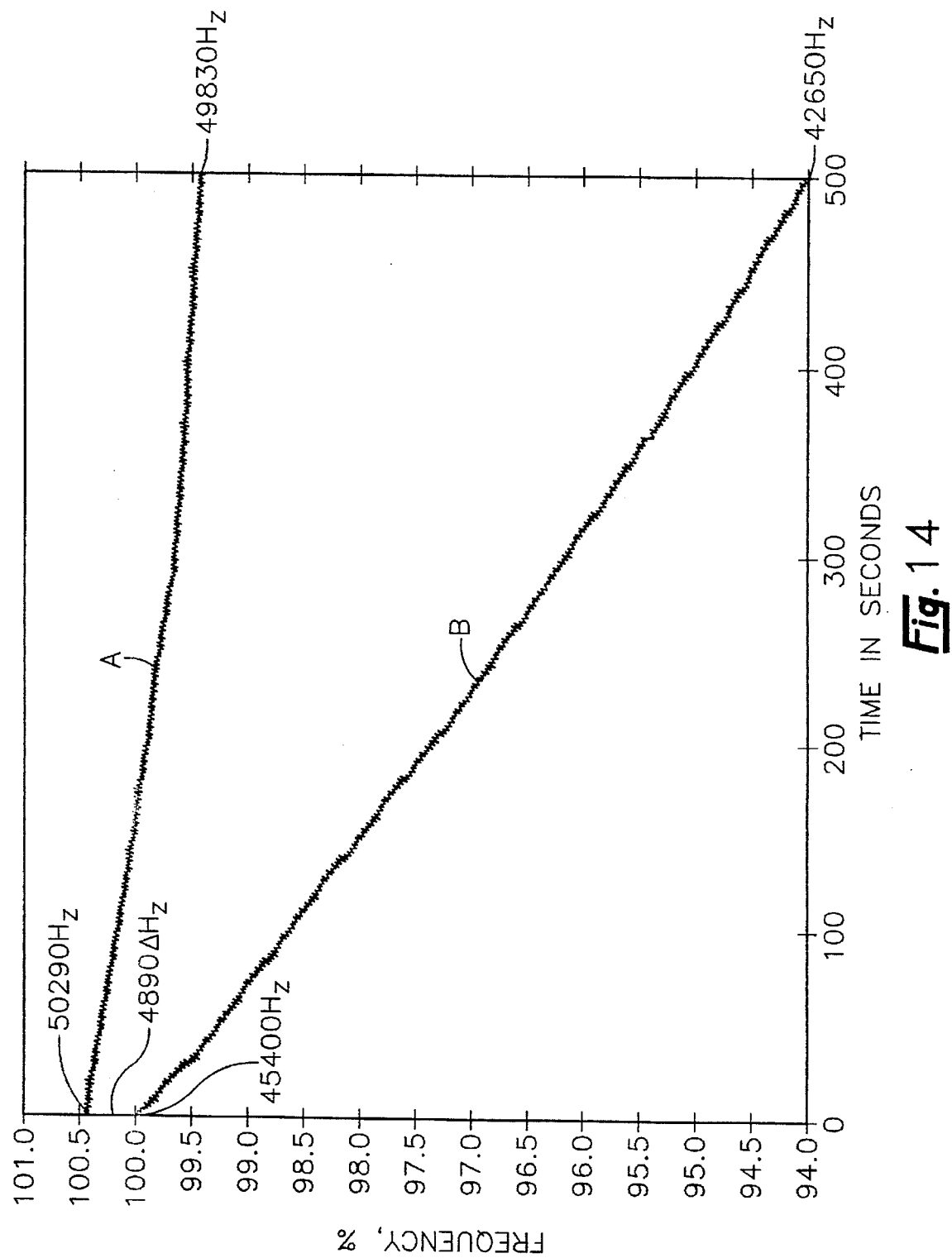
FIG. 14 is a graph of frequency vs time data taken by the invention from a stern oil having approximately 11.0% water entrained therewith.

An uncontaminated sample of stern oil is the subject of Test No. 26, the data from which is reported as plot A of FIG. 14. The initial frequency is 50,290 Hz which declines over the 500 second test interval to 49,830 Hz: a difference of 460 Hz (col. H).

EXAMPLE VII

Plot B of FIG. 14 reports the data of Test No. 29 which is of a stern oil contaminated with 11% water. The initial natural frequency of the sample is 45,400 Hz and declines to 42,650 Hz over the 500 second test interval. Such initial natural frequency of 45,400 Hz is 4890 Hz less than the 50,290 Hz initial natural frequency of the uncontaminated Test No. 26 sample. This initial natural frequency differential is combined with the water solution affinity rate of $18.0 \times 10^{-4}\%$ $H_2O$/Hz (col. I) to calculate the dissolved water content of 8.802% $H_2O$.

Expansively:

4890 Hz×$18.0 \times 10^{-4}\%$ $H_2O$/Hz=8.802% $H_2O$ dissolved

Plot B is substantially smooth, continuous and without anomaly. It is, therefore, assumed there is no free water in the sample. The quantity of emulsified water, however, is determined from the gross frequency decline of 2750 Hz between the initial natural frequency of 45,400 Hz and the final frequency of 42,650 Hz corrected by the 460 Hz characteristic decline of uncontaminated oil. Combining this frequency difference with the emulsified water affinity rate of $9.0 \times 10^{-4}\%$ $H_2O$/Hz (col. J), the sample of Test No. 29 is calculated to contain 2.061% $H_2O$ emulsified.

Expansively:

2290 Hz×$9.0 \times 10^{-4}\%$ $H_2O$/Hz=2.061% $H_2O$ emulsified

Collectively, therefore, the total water present in the Test No. 29 sample is:

|   | 8.802% | $H_2O$ Dissolved |
|---|---|---|
| + | 2.061% | $H_2O$ Emulsified |
|   | 10.863% | $H_2O$ Total |

Although a preferred embodiment is described herein, it will be understood that the invention is capable of numerous modifications, rearrangements and substitutions of parts without departing from the scope of the invention as defined in the following claims. For example, particular oil borne contaminants have substantially unique, frequency dependent dielectric properties that may be identified by incremental or sweep variations in the sensor 16 input signal frequency. Useful data may also be acquired by measuring the phase shift of a sensor 16 signal in the microwave frequency range.

As our invention we claim:

1. Method of approximating the proportionate quantity of water emulsified in a contaminated sample of a subject oil, said method comprising the steps of:

preparing a first data base with a correlation between a rate of change in an electrical property of an oil subject type over a predetermined time and a percentage of water emulsified within such subject type oil;

identifying a contaminated test oil sample as being of said subject type oil by making a comparison of a measured rate of change of said electrical property on said contaminated test oil sample against said rates data base having many different said rates of change in said electrical property;

preparing a second data base by measuring the relative rate of change in said electrical property over a predetermined time respective to said test oil sample; and concluding an approximate percentage of water emulsified in said contaminated test oil sample by applying the correlation of said first data base to said second data base.

2. A method of approximating the proportionate quantity of free water in a contaminated sample of subject oil, said method comprising the steps of:

preparing a first data base with a correlation between abrupt variations in an electrical property of an oil of a subject type and a percentage of free water within such subject type oil;

identifying a contaminated test oil as being of said subject type oil by making a comparison of a measured rate of change of said electrical property on said contaminated test oil sample against said first data base having many different said rates of change in said electrical property;

measuring abrupt variations in the rate of change in said electrical property over time for a settling sample of said contaminated test oil; and, concluding an approximate percentage of free water in the contaminated sample by applying said abrupt electrical property changes to said correlation.

3. A method of approximating the proportionate quantity of total water present in a sample of test oil, said method comprising the steps of:

establishing a first correlation between a change in oil electrical properties and a percentage of water dissolved therein respective to a test oil;

establishing a second correlation between a change in oil electrical properties and a percentage of water emulsified or dispersed therein respective to said test oil;

establishing a third correlation between a change in oil electrical properties and a percentage of free water therein respective to said test oil;

obtaining a first measured data set of electrical property values for an uncontaminated sample of said test oil taken over a predetermined time and temperature change starting with a first initial value;

obtaining a second measured data set of electrical property values for a contaminated sample of said test oil taken over said predetermined time and temperature change starting with a second initial value;

measuring abrupt variations in a rate of change in electrical property values over time for a settling contaminated sample of said test oil;

concluding an approximate percentage of dissolved water in said contaminated sample by applying said first correlation to a net difference between said first and second initial electrical property values;

measuring a rate of change in said electrical property value for a contaminated sample of said test oil;

concluding an approximate percentage of water emulsified in said contaminated sample by applying said second correlation to a net difference between said second initial value and a final electrical property value for said contaminated sample;

concluding an approximate percentage of free water in the contaminated sample by applying said third correlation to said abrupt variations in said rate of changes in said electric property value; and, approximating the total water presence in said sample by summing the approximate percentages of dissolved, emulsified or dispersed and free water concluded to be present therein.

4. A method as described by claims 3 wherein a drying agent is combined with said uncontaminated sample of test oil for obtaining said first measured data set.

5. A method of approximating the proportionate quantity of water combined in a reference quantity of test oil, said method comprising the steps of;

respective to an uncontaminated sample of test oil, determining the natural frequency response as a measure of relative dielectric value;

respective to a contaminated sample of said test oil, determining as a change in frequency response with respect to time, a change in relative dielectric value;

establishing a correlation between said changes in said test oil frequency response of relative dielectric value and a percentage of water present in said test oil;

comparing said contaminated test oil frequency response to said uncontaminated test oil frequency response of relative dielectric value to determine a frequency response differential; and, concluding an approximate percentage of water presence in said contaminated test oil by applying said correlation to said frequency response differential.

6. A method as described by claim 5 wherein a correlation is established between the relative quantity of water that is in solution with additives mixed with said test oil and the natural frequency difference between an uncontaminated sample of said test oil and a contaminated sample of said test oil.

7. A method as described by claim 5 wherein a correlation is established between the relative quantity of water that is emulsified with said test oil and the net natural frequency difference between an uncontaminated sample of said test oil and a contaminated sample of said test oil.

8. A method as described by claim 5 wherein said natural frequency response is determined from an uncontaminated sample of test oil mixed with a drying agent.

9. A method of approximating the proportionate quantity of water combined in a reference quantity of test oil, said method comprising the steps of:

respective to an uncontaminated sample of test oil, determining, as a change in frequency response, a change in the test oil relative dielectric value with respect to time;

respective to a contaminated sample of said test oil, determining, as a change in frequency response, a change in the test oil relative dielectric value with respect to time;

establishing a correlation between frequency response change in said uncontaminated test oil and a percentage of water in said uncontaminated test oil;

comparing said contaminated test oil frequency response to said uncontaminated test oil frequency response of relative dielectric value to determine a frequency response differential; and, concluding an approximate percentage of water presence in said contaminated test oil by applying said correlation to said frequency response differential.

10. A method as described by claim 9 wherein a drying agent is mixed with said uncontaminated sample of test oil.

11. A method of approximating the proportionate quantity of water combined with a reference quantity of test oil, said method comprising the step of:

energizing an open grid capacitor with an oscillator at a frequency dependent upon the capacitance of said capacitor;

confining a substantially uncontaminated sample of test oil in wet surface contact with the energized open grid of said capacitor;

energizing an electromagnet disposed beneath said capacitor to emit a magnetic field through said uncontaminated oil sample confined to wet surface contact with said energized capacitor grid;

measuring and recording said oscillator frequency at least at the beginning and end of a standard time interval elapsed from the energized start of said magnetic field through said uncontaminated oil sample as a first data set;

confining a contaminated sample of said test oil in wet surface contact with said energized capacitor;

energizing said electromagnet to emit a magnetic field through said contaminated oil sample in wet surface contact with said energized capacitor;

measuring and recording said oscillator frequency at least at the beginning and end of said standard time interval as a second data set;

establishing a correlation between oscillator frequency change and a percentage quantity of water in said test oil;

comparing said second data set to skid first data set to determine the oscillator frequency differentials there between; and, applying said correlation between, frequency change and water quantity to determine the approximate water quantity combined with said contaminated test oil.

12. A method as described by claim 11 wherein the oscillator frequency differential between said first and second data sets relative to the beginning of said standard time interval is presumed to substantially represent water in solution with oil additives.

13. A method as described by claim 11 wherein that percentage of water combined with Said contaminated test oil represented by the oscillator frequency differential between said first and second data sets at the beginning of said standard time interval is presumed as substantially combined with oil additives as a solution.

14. A method as described by claim 11 wherein that percentage of water combined with said contaminated test oil represented by the oscillator frequency differential between said first and second data sets at the end of said standard time interval is the approximate total of combined water in all forms.

15. A method as described by claim 11 wherein said uncontaminated sample of test oil is mixed with a drying agent.

16. A method of classifying the utility type of a substantially uncontaminated lubricating oil with respect to additive content, said method comprising the steps of:

energizing an open capacitor sensor to produce an ouput signal dependent upon the capacitance of said capacitor sensor;

confining a substantially uncontaminated sample of test oil having an unknown additive content in wet surface contact with said capacitor;

energizing a heating means adjacent to said test oil sample while confined to wet Surface contact with said energized capacitor;

measuring and recording said capacitor sensor output signal at predetermined intervals over a standard elapsed time period from an energized start of said heating means to generate a first sensor output signal Vs time functional relationship for said test oil sample;

comparing said first functional relationship of said test oil sample to at least one second functional relationship corresponding to said first relationship respective to a reference oil of substantially known additive content; and, concluding from said comparison that the additive content of said test oil is substantially the same as said reference oil.

* * * * *

UNITED STATES PATENT AND TRADEMARK OFFICE
CERTIFICATE OF CORRECTION

PATENT NO. : 5,656,767
DATED : Aug. 12, 1997
INVENTOR(S) : Raymond E. Garvey, III, and Alexander Andrew Carey It is certified that error appears in the above-indentified patent and that said Letters Patent is hereby corrected as shown below:

Column 4, line 24 following "number", delete "of" and insert --or-- therefor.

Column 20, line 3, correct the formulated number to read --0.19734--.

Column 23, line 19, delete "rates" and insert --first-- therefor.

Column 26, line 10, correct the spelling of "said" with a lower case --s--.

Column 26, line 34, correct the spelling of "surface" with a lower case --s--.

Column 26, line 40, correct the spelling of "Vs" thusly --vs--.

Signed and Sealed this

Seventh Day of October, 1997

Attest:

BRUCE LEHMAN

Attesting Officer     Commissioner of Patents and Trademarks